(12) United States Patent
Bagga et al.

(10) Patent No.: US 8,608,802 B2
(45) Date of Patent: Dec. 17, 2013

(54) IMPLANTABLE DEVICES FOR SUBCHONDRAL TREATMENT OF JOINT PAIN

(75) Inventors: Charanpreet S. Bagga, Basking Ridge, NJ (US); Shaun B. Hanson, West Chester, PA (US); Christopher D. Mandeen, Bethlehem, PA (US); Michael J. Simpson, West Chester, PA (US); Steven B. Cohen, Media, PA (US); Charles F. Leinberry, Chester Springs, PA (US); Peter F. Sharkey, Villanova, PA (US)

(73) Assignee: Zimmer Knee Creations, Inc., West Chester, PA (US)

( * ) Notice: Subject to any disclaimer, the term of this patent is extended or adjusted under 35 U.S.C. 154(b) by 84 days.

(21) Appl. No.: 12/950,306

(22) Filed: Nov. 19, 2010

(65) Prior Publication Data

US 2011/0125265 A1 May 26, 2011

Related U.S. Application Data

(60) Provisional application No. 61/263,170, filed on Nov. 20, 2009, provisional application No. 61/292,979, filed on Jan. 7, 2010, provisional application No. 61/300,337, filed on Feb. 1, 2010, provisional application No. 61/324,931, filed on Apr. 16, 2010.

(51) Int. Cl.
*A61F 2/28* (2006.01)

(52) U.S. Cl.
USPC .......................................... 623/16.11; 606/62

(58) Field of Classification Search
CPC ................................. A61F 2/28; A61B 17/72

USPC ........... 623/16.11; 128/92; 606/72, 73, 62, 63
See application file for complete search history.

(56) References Cited

U.S. PATENT DOCUMENTS

| 4,653,487 | A  | 3/1987  | Maale        |
|-----------|----|---------|--------------|
| 5,370,646 | A  | 12/1994 | Reese et al. |
| 5,514,137 | A  | 5/1996  | Coutts       |
| 5,556,429 | A  | 9/1996  | Felt         |
| 5,755,809 | A  | 5/1998  | Cohen        |
| 6,140,452 | A  | 10/2000 | Felt         |
| 6,235,043 | B1 | 5/2001  | Reiley       |
| 6,241,734 | B1 | 6/2001  | Scribner     |
| 6,248,110 | B1 | 6/2001  | Reiley       |
| 6,306,177 | B1 | 10/2001 | Felt         |
| 6,395,007 | B1 | 5/2002  | Bhatnagar    |
| 6,564,083 | B2 | 5/2003  | Stevens      |
| 6,607,561 | B2 | 8/2003  | Brannon      |

(Continued)

OTHER PUBLICATIONS

May 12, 2008 Riddle Memorial Hospital, Medial, PA 19063 Operative Report. Surgeon: Peter F Sharkey, M.D.; Right knee, medial tibial plateau; A cannulated bone biopsy needle was placed into the bone under fluoroscopic guidance; Implant used: Stryker Orthopedics Hydroset (Bone Substitute Material); Surgeon also expressed difficulty in injecting the bone substitute.

(Continued)

*Primary Examiner* — Jason-Dennis Stewart
(74) *Attorney, Agent, or Firm* — Monument IP Law Group

(57) ABSTRACT

Devices and associated methods are disclosed for treating bone, and particularly bone tissue at the joints. Disclosed are implantable devices that can be used either alone or in combination with this augmentation or hardening material for the repair of bone defects and which are particularly suited for use at the joints, and even more particularly, suited for use at the subchondral bone level.

21 Claims, 26 Drawing Sheets

(56) References Cited

U.S. PATENT DOCUMENTS

| | | |
|---|---|---|
| 6,613,054 B2 | 9/2003 | Scribner |
| 6,719,761 B1 | 4/2004 | Reiley |
| 6,746,451 B2 | 6/2004 | Middleton |
| 6,827,720 B2 | 12/2004 | Leali |
| 6,863,899 B2 | 3/2005 | Koblish |
| 6,887,246 B2 | 5/2005 | Bhatnagar |
| 7,153,307 B2 | 12/2006 | Scribner |
| 7,261,720 B2 | 8/2007 | Stevens |
| 7,708,742 B2 | 5/2010 | Scribner |
| 7,771,431 B2 | 8/2010 | Scribner |
| 7,811,290 B2 | 10/2010 | Rabiner |
| 8,152,813 B2 | 4/2012 | Osorio |
| 8,168,692 B2 | 5/2012 | Wenz |
| 2003/0105468 A1 | 6/2003 | Gorek |
| 2003/0138473 A1 | 7/2003 | Koblish |
| 2004/0106925 A1 | 6/2004 | Culbert |
| 2005/0119219 A1 | 6/2005 | Bellini |
| 2006/0064164 A1 | 3/2006 | Theien |
| 2010/0076503 A1 | 3/2010 | Beyar |
| 2010/0179549 A1 | 7/2010 | Keller |

OTHER PUBLICATIONS

Oct. 27, 2008 SPU Operative Report. Surgeon: Steven B Cohen, M.D.; An Anterior Cruciate Ligament (ACL) portal-creation device was repurposed for this surgery; The tibial probe was placed on the medial femoral condyle, with the tunnel guide secured proximally on the thigh; The surgeon expressed difficulty in positioning and stabilizing the guide; A cannulated pin was placed through the tunnel guide and placed distally into the medial femoral condyle; No implant was injected into the bone.

Nov. 10, 2008 SPU Operative Report. Surgeon: Steven B Cohen, M.D.; Treatment of the central medial tibial plateau; A guide pin was inserted into the medial tibial plateau; An endo button drill bit was used to expand the drill hole; One cubic centimeter (cc) of cement was inserted into the bone; A second drill hole was made from below, and a second cc was inserted into the bone.

IMPLANTABLE DEVICES FOR SUBCHONDRAL TREATMENT OF JOINT PAIN

CROSS REFERENCE TO RELATED APPLICATIONS

This application claims priority to U.S. Provisional No. 61/324,931 filed Apr. 16, 2010, and entitled "Implantable Devices for Treating Bone Defects," U.S. Provisional No. 61/300,337 filed Feb. 1, 2010, and entitled "DEVICES AND INSTRUMENTS FOR BONE REPAIR AND METHODS OF USE," U.S. Provisional No. 61/292,979 filed Jan. 7, 2010, and entitled "Instruments and Implants for Joint Repair and Methods of Use," and U.S. Provisional No. 61/263,170 filed Nov. 20, 2009, and entitled "METHOD FOR TREATING JOINT PAIN AND ASSOCIATED INSTRUMENTS," which are herein incorporated by reference in their entirety.

This application also relates to co-pending and co-owned U.S. patent application Ser. No. 12/950,355, filed Nov. 19, 2010 and entitled "SUBCHONDRAL TREATMENT OF JOINT PAIN," U.S. patent application Ser. No. 12/950,273, filed Nov. 19, 2010 and entitled "IMPLANTABLE DEVICES FOR SUBCHONDRAL TREATMENT OF JOINT PAIN," the content of which is herein incorporated in its entirety by reference.

FIELD

The present invention relates to devices and instruments for the surgical treatment of bone tissue, and more particularly to devices, instruments and associated methods for the surgical repair and treatment of damaged or compromised bone tissue, especially at or near a joint.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in the knee, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

One of the difficulties of currently available devices and instruments is the lack of ability to control the injection of a hardening or augmentation material into bone. Oftentimes, the injectable material spreads out too much from its intended site, or is prone to backflow out of the bone or injection device. Further, where the bone defect occurs at, or near, a joint region, the mechanical fixation devices need to be appropriately sized and configured to be easily inserted quickly and precisely so as to avoid creating further trauma during its delivery.

Accordingly, it is desirable to provide devices and instruments that can allow precise, controlled injection of an augmentation or hardening material into bone. It is further desirable to provide implantable devices that can be used either alone or in combination with this augmentation or hardening material for the repair of bone defects, particularly at the joints, and even more particularly at the subchondral bone level.

SUMMARY

The present disclosure provides devices and instruments that can allow precise, controlled injection of an augmentation or hardening material into bone. Also provided are implantable devices that can be used either alone or in combination with this augmentation or hardening material for the repair of bone defects and which are particularly suited for use at the joints, and even more particularly suited for use at the subchondral bone level.

In one exemplary embodiment, an implantable device for insertion into bone is provided. The device may include an elongate body extending between a first, leading end and a second, trailing end, the second end including a tool-receiving portion for receiving a tool, the elongate body including a central canal for receiving a flowable material, and having one or more channels in fluid communication with the central canal. The device may further include flutes on the elongate body. The one or more channels may be located on one side of the device, and may further reside within a recess along the elongate body.

In another exemplary embodiment, a system for treating a bone defect is provided. The system may include an implantable device for insertion into bone, the device comprising an elongate body extending between a first, leading end and a second, trailing end, the second end including a tool-receiving portion for receiving a tool, the first end having a tapered tip, the elongate body including a central canal for receiving an injection tool, and having one or more channels in fluid communication with the central canal. The system may also include an injection tool having a hollow shaft configured for insertion through the central canal of the implantable device, the shaft being capable of receiving a flowable material, and further including one or more channels configured to align with one or more channels of the implantable device to allow extrusion of the flowable material out of the injection tool and through the one or more channels of the implantable device.

In yet another exemplary embodiment, a system for treating a bone defect is provided. The system may include a flowable material delivery device for insertion into bone, the device comprising a threaded elongate body extending between a first, leading end and a second, trailing end, the second end including a tool-receiving portion for receiving a tool, the elongate body including a central canal for receiving a flowable material, and having one or more channels in fluid communication with the central canal. The system may further include an inserter tool having a handle extending into a shaft and terminating at a device-attachment end, the device-attachment end being configured to attach to the second end of the delivery device. A protection sleeve may also be provided. The protection sleeve may include a tubular body having a handle at one end, and terminating at a bone-contacting surface at an opposite end, the tubular body including a threaded channel configured to threadedly receive the delivery device.

In still yet another exemplary embodiment, a method of treating a bone defect is provided. The method includes the step of providing a first implantable device for insertion into bone, the device comprising an elongate body extending between a first, leading end and a second, trailing end, the second end including a tool-receiving portion for receiving a tool, the elongate body including a central canal for receiving a flowable material, and having one or more channels in fluid communication with the central canal. The method also includes providing a second implantable device for insertion into bone, the device comprising an elongate body extending between a first, leading end and a second, trailing end, the second end including a tool-receiving portion for receiving a tool, the elongate body including a central canal for receiving a flowable material, and having one or more channels in fluid communication with the central canal. Next, the first and second implantable devices may be implanted such that one or more channels of each device is aligned. Flowable material may be injected into at least one of the implantable devices.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1A:
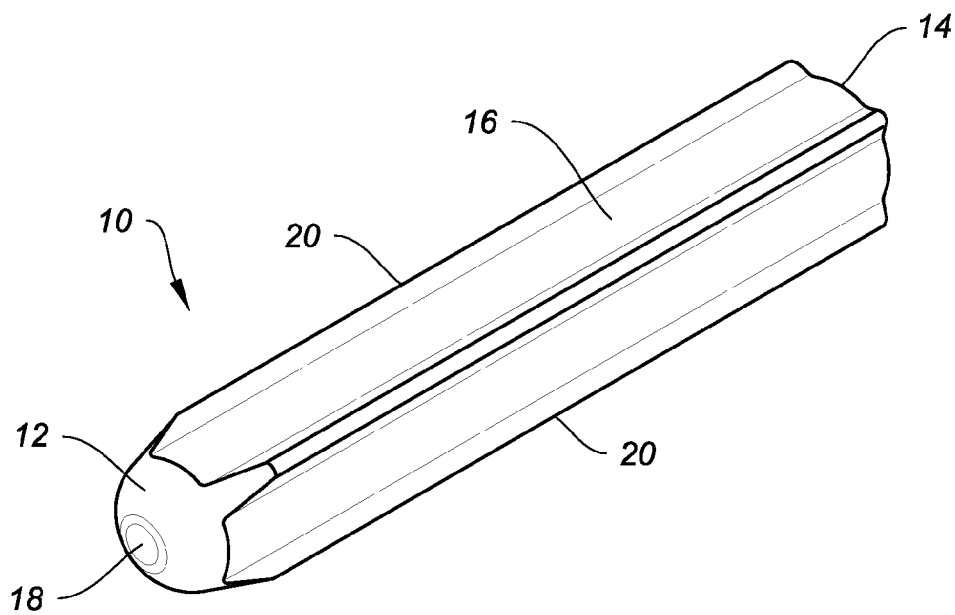
FIG. 1A is a perspective view of an exemplary embodiment of an implantable device of the present invention.

The present disclosure provides a methodology, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, the embodiments diagnose and treat pain at its source in the subchondral region of a bone of a joint to relieve the pain. Applicants have discovered that pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Applicants have discovered that treatment of the bone by mechanical and biological means to restore the normal physiologic stress distribution, and restore the healing balance of the bone tissue at the subchondral level, is a more effective way of treating pain than conventional techniques. That is, treatment can be effectively achieved by mechanically strengthening or stabilizing the defect, and biologically initiating or stimulating a healing response to the defect. Accordingly, the present disclosure provides methods, devices, and systems for a subchondral procedure. This procedure and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In SCP™, bone fractures or non-unions are stabilized, integrated or healed, which results in reduction of a bone defect, such as a bone marrow lesion or edema. In addition, SCP™ restores or alters the distribution of forces in a joint to thereby relieve pain. SCP™ can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY™ generally comprises evaluating a joint, for example, by taking an image of the joint, detecting the presence of one or more subchondral defects, diagnosing which of these subchondral defects is the source of pain, and determining an extent of treatment for the subchondral defect. The present technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. The present disclosure provides several exemplary treatment modalities for SCP™ for the different extents of treatment needed. Accordingly, a medical practitioner may elect to use the techniques and devices described herein to subchondrally treat any number of bone defects as he deems appropriate.

In some embodiments, detection and identification of the relevant bone marrow lesion or bone marrow edema (BML or BME) can be achieved by imaging, e.g., magnetic resonance imaging (MRI), X-ray, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface or periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatments can be administered on acute stress fractures, BML or BME, or other subchondral defects, as previously mentioned.

According to the embodiments, the SCP™ treatment may continue after surgery. In particular, the patient may be monitored for a change in pain scores, or positive change in function. For example, patients are also checked to see when they are able to perform full weight-bearing activity and when they can return to normal activity. Of note, if needed, the SCP™ procedure can be completely reversed in the event that a patient requires or desires a joint replacement or other type of procedure. The SCP™ treatment may also be performed in conjunction with other procedures, such as cartilage resurfacing, regeneration or replacement, if desired.

The present disclosure provides a number of treatment modalities, and associated devices, instruments and related methods of use for performing SUBCHONDROPLASTY™. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implant may be placed in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument. Exemplary guide instruments, navigation, and targeting systems are also disclosed in co-pending and co-owned U.S. patent application Ser. No. 12/950,230, filed Nov. 19, 2010 and entitled "INSTRUMENTS FOR TARGETING A JOINT DEFECT;" U.S. patent application Ser. No. 12/950,154, filed Nov. 19, 2010 and entitled "INSTRUMENTS FOR VARIABLE ANGLE APPROACH TO A JOINT;" U.S. patent application Ser. No. 12/950,114, filed Nov. 19, 2010 and entitled "COORDINATE MAPPING SYSTEM FOR A JOINT TREATMENT," U.S. patent application Ser. No. 12/950,061, filed Nov. 19, 2010 and entitled "NAVIGATION AND POSITIONING INSTRUMENTS FOR JOINT REPAIR," the contents of which are herein incorporated in their entirety by reference.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Accordingly, the present disclosure also provides suitable implantable fixation devices for the surgical treatment of these altered bone regions or bone defects, especially at the subchondral level. Applicants have also discovered devices and instruments that can be used in combination with cements or hardening materials commonly used to repair damaged bone by their introduction into or near the site of damage, either to create a binding agent, cellular scaffold or mechanical scaffold for immobilization, regeneration or remodeling of the bone tissue.

Turning now to the drawings, mechanical fixation devices particularly suitable for implantation in certain areas of the bone, such as the periarticular surface or the subchondral bone area (usually within the range of about 2-15 mm from the bone surface) are shown. Referring now to FIG. 1A, an exemplary embodiment of an implantable device of the present disclosure is shown. Implant 10 can include an elongate body 16 extending between a proximal, leading end 12 and a distal, trailing end 14. The distal end 14 may include a tool-receiving portion (not shown) for receiving a tool, such as an insertion tool (not shown in FIG. 1A). The proximal end 12 of the implant 10 can include a tapered nose or tip 18 to facilitate ease of insertion to the target site.

In addition, a surface feature may be present on the elongate body 16 for enhanced bone tissue engagement with the target site. In the embodiment shown, the surface feature may comprise a fin 20. One or more fins 20 can be provided in the present embodiment. The fins 20 of FIG. 1A may have a uniform height across their length, or the fins 20 may have varying heights across their length to create a curved, wavy, or irregular pattern. For example, the fins 20 may be S-shaped, V or W-shaped to create a jagged spine-like profile along the length of the elongate body 16. It is contemplated that the surface feature may also include structural elements such as teeth, barbs, bumps, spikes, or other surface enhancements.

While the elongate body 16 is shown as being substantially cylindrical, it is understood that the elongate body 16 may be shaped so as to have varying diameters along its length. For instance, the elongate body 16 may have a figure "8" shape, a bowling pin shape, a U-shape, a crescent or C-shape, an I-beam shape, a rectangular or square shape, a star shape, or corkscrew shape, etc. so long as it is suitable for insertion into bone tissue and has enough structural integrity to perform its intended function of bridging a fracture or fissure, supporting bone regrowth or remodeling, and/or binding the bone tissue together to prevent further breakdown or degeneration.

If desired, the surface feature may include a biological agent. The biological agent may be included in a coating on the implant 10. Alternatively, the biological agent may be embedded inside the implant 10. Suitable biological agents may include, for example, osteogenic, osteoconductive and/ or osteoinductive agents. In addition, a bioactive agent such as platelet rich plasma, for example, may also be employed. Furthermore, a bioactive surface may be created on the implant 10 by treating the implant 10 with, for example, acid etching, grit blasting, plasma spraying, or other suitable surface treatments.

The implant 10 may be formed of any suitable biocompatible material, including metal or polymer materials. Suitable metals may include, but are not limited to, stainless steel, titanium, titanium alloys, and cobalt chrome, as examples. Porous metals may also be appropriate. The implant 10 may also be ABS injection molded plastic, polyetheretherketone (PEEK), polyethylene (PE), or ultra high molecular weight polyethylene (UHMWPE). If desired, the implant 10 may be bioabsorbable or bioresorbable. In some embodiments, the implant 10 may be formed of allograft or cadaver bone, including cortical, cortico-cancellous, bi-cortical, tri-cortical, or sesamoid bone material. In other embodiments, the implant 10 may be formed of a radiolucent material. In addition, radiopaque markers may be employed with the implant 10 for imaging possibilities.

Figure 1B:
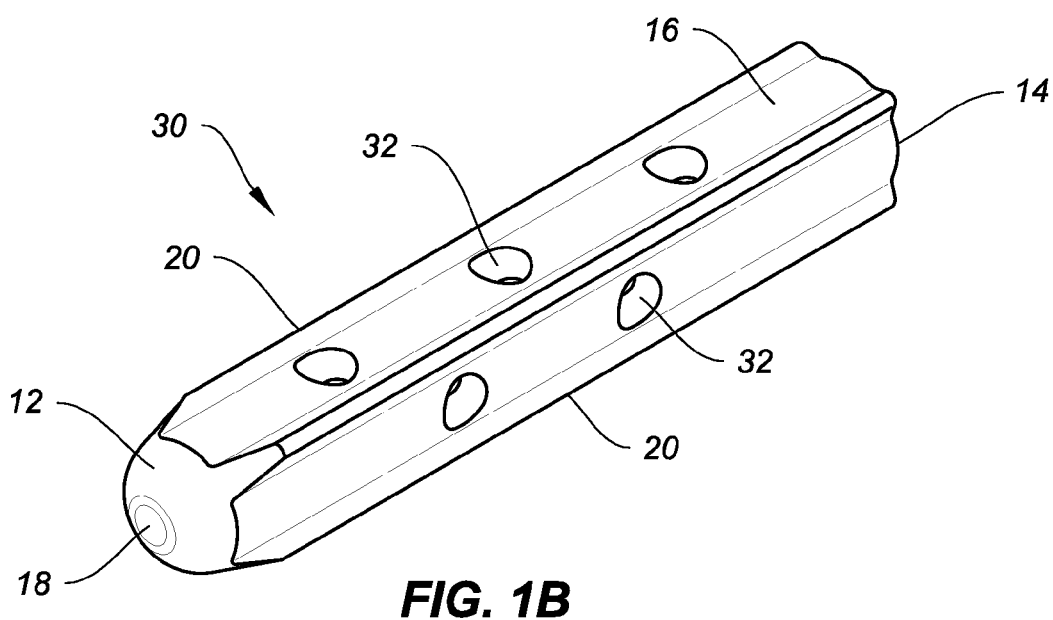
FIG. 1B is a perspective view of another exemplary embodiment of an implantable device of the present invention.

FIG. 1B illustrates another exemplary embodiment of an implantable device of the present disclosure, where the fenestrated implant 30 has the same elements as implant 10 (with like numerals designating the same elements) and further includes side channels 32 extending through the elongate body 16. One or more pores or side channels 32 can be provided. The fenestrated implant 30 may include a central channel (not shown) for receiving a fluidic material, such as a bone void filler or bone cement. The central channel may be in fluid communication with the side channels 32 to allow excess material injected into the implant 30 to seep or ooze out and around the elongate body. Additionally, the side channels 32 may allow some tissue growth into the implant 30 through these same channels 32. If desired, additional perforations may be provided to allow better fluid transfer through the implant 30, and further may allow vessels to grow through the perforations.

Figure 1C:
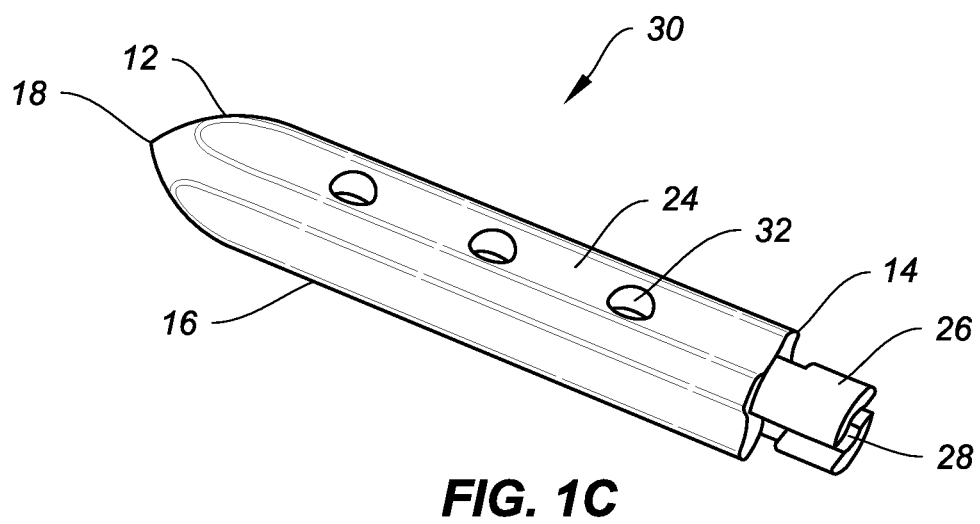
FIG. 1C is a perspective view of another exemplary embodiment of an implantable device of the present invention.

FIG. 1C illustrates another exemplary embodiment of a device of the present disclosure. In similar fashion to the embodiments shown in FIGS. 1A and 1B, implant 30 can include an elongate body 16 extending between a first, leading end 12 and a second, trailing end 14. The second end 14 may include tabs 26 to for receiving an insertion tool (not shown). The first end 12 of the implant 10 can include a tapered nose or tip 18 to facilitate ease of insertion to the target site. For example, as shown, the tip 18 may have a relatively sharper tapered tip or bullet-like nose in order to facilitate insertion of the implant 30.

The elongate body 16 may further include recesses or flutes 24 extending along the longitudinal axis of the implant 30 and around the circumference of the elongate body 16. The implant 30 may be provided with a central opening or canal 28 extending longitudinal along the major axis, as shown, or it may be cannulated as is common in the art. Although shown with a closed tip 18, it is envisioned that the tip 18 may be open if desired, so as to allow the implant 30 to slide entirely over a guide wire for insertion. Further, the implant 30 may be fenestrated, with pores or channels 32 also provided on the flutes 20. The pore or channels 32 may be in fluid communication with the central opening 28 of the implant 30.

As previously mentioned, the implant 30 may further be augmented with a PMMA or CaP cement injection, other biologic agent, or an osteoconductive, osteoinductive and/or osteogenic agent like a bone graft material. The augmentation material may be introduced through the implant, around the implant, and/or apart from the implant but at the affected bone region, such as into the lower region of a bone marrow lesion. For example, the implant may act as a portal to inject the augmentation material into the bone tissue.

The present embodiment provides structural features to accommodate these scenarios. It is contemplated that the second end 14 of the implant 30 may be configured to allow a quick release connection with a tool, such as for example a threaded connection. As shown, the tabs 26 on the second end 14 provide a simple and quick mechanism for attachment to an insertion tool or even an injection system. The tool could be, for example, an insertion tool, an injection needle, or a catheter. In one embodiment, the tabs 26 can create a bayonet-type connection whereby the implant 30 can be inserted and twisted to lock into the tool or system. Alternatively, the implant 30 may be provided with a Luer lock-type mechanism for attachment to an injection system. The central opening 28 would enable the augmentation material to be introduced through the implant 30, while the channels 32 would allow the material to be ejected around the implant 30. The flutes 24 around the elongate body 16 create voids or open space around the implant 30 to accommodate the augmentation material. The pores or channels 32 can also provide access for bone ingrowth and vasculature permeation. The pores or channels 32 may be provided in any variety of sizes; however, it is understood that adjustment of the pore size would allow the user to control the flow of an injectable material through the implant 30. By making the pores 32 smaller, resistance to flow is increased and alternatively by making the pores 32 larger, resistance to flow is reduced. It is therefore contemplated that the implant 30 may be provided with suitably sized pores 32 for use with the intended injectable material desired. For instance, the pores or channels 32 may have a larger dimension than the central opening 28, creating a path of least resistance for injected material through the channels 32 and thereby reducing backflow out of the central opening 28.

As further shown, it is possible to provide an implant 30 with the channels 32 in only region of the elongate body 16. FIG. 1C illustrates an implant 30 whereby the channels (or pores) 32 are located along one side of the implant 30 to allow the user to control the directionality and flow of the injectable material to be used. In one example, the implant 30 may be inserted so that the channels 32 face towards a bone defect. When an injectable material is introduced into the implant 30 and allowed to extrude from the channels 32, it is possible to inject in such a way to enable the material to bounce off the surface of the bone defect and subsequently surround the implant 30. Although not shown, it is contemplated that a plug or cap may be provided with implant 30 in order to seal off the central opening 28 and thereby prevent any augmentation material contained within to leak out.

In similar fashion as implant 10, the implant 30 may be formed of any suitable biocompatible material, including metal or polymer materials. Suitable metals may include, but are not limited to, stainless steel, titanium, titanium alloys, and cobalt chrome, as examples. Porous metals may also be appropriate. The implant 30 may also be ABS injection molded plastic, polyetheretherketone (PEEK), polyethylene (PE), or ultra high molecular weight polyethylene (UHMWPE). If desired, the implant 30 may be bioabsorbable or bioresorbable. In some embodiments, the implant 30 may be formed of allograft or cadaver bone, including cortical, cortico-cancellous, bi-cortical, tri-cortical, or sesamoid bone material. In other embodiments, the implant 30 may be formed partially or wholly from a radiolucent material. For example, the implant may be formed from a material blended with a radiopaque material, such as barium sulfate. In addition, radiopaque markers may be employed with the implant 30 for imaging possibilities.

While the elongate body 16 is shown as being substantially cylindrical, it is understood that the implant 30 may be shaped so as to have varying diameters along its length. For instance, the implant 30 may have an overall threaded configuration, a figure "8" shape, a bowling pin shape, a U-shape, a crescent or C-shape, an I-beam shape, a rectangular or square shape, a star shape, or corkscrew shape, etc. so long as it is suitable for insertion into bone tissue and has enough structural integrity to perform its intended function of bridging a fracture or fissure, supporting bone regrowth or remodeling, and/or binding the bone tissue together to prevent further breakdown or degeneration.

The implants 10, 30 of the present disclosure may be used to repair bone defects in a joint region such as the knee, shoulder, ankle, hip or other joint of the patient's body. The implants may be useful, for example, in repairing an insufficiency fracture of a bone at a joint. The implants may serve as a fusion device, enabling rigid fixation at the defect site. For instance, the implants may serve as a useful facet fusion device. Alternatively, the implants may be configured to facilitate the patient's natural healing process without fusion at the defect site.

If desired, the implants 10, 30 may also include a biological agent. The biological agent may be included in a coating on the implants 10, 30. Alternatively, the biological agent may be embedded inside the implants 10, 30. Suitable biological agents may include, for example, osteogenic, osteoconductive and/or osteoinductive agents. In addition, a bioactive agent such as platelet rich plasma (PRP), bone marrow aspirate (BMA), bone morphogenic protein (BMP), demineralized bone matrix (DBM), stem cells, or allograft material, for example, may also be employed. Furthermore, a bioactive surface may be created on the implants 10, 30 by treating the implant 10, 30 with, for example, acid etching, grit blasting, plasma spraying, bioactive glass coating, photo-chemical etching, or other suitable surface treatments for creating a roughened surface. While the implants have been described as being used with an injectable material, it is understood, however, that the implants shown here, as well as the other implants and devices described herein, may be used alone without any injectable material.

Figure 2A:
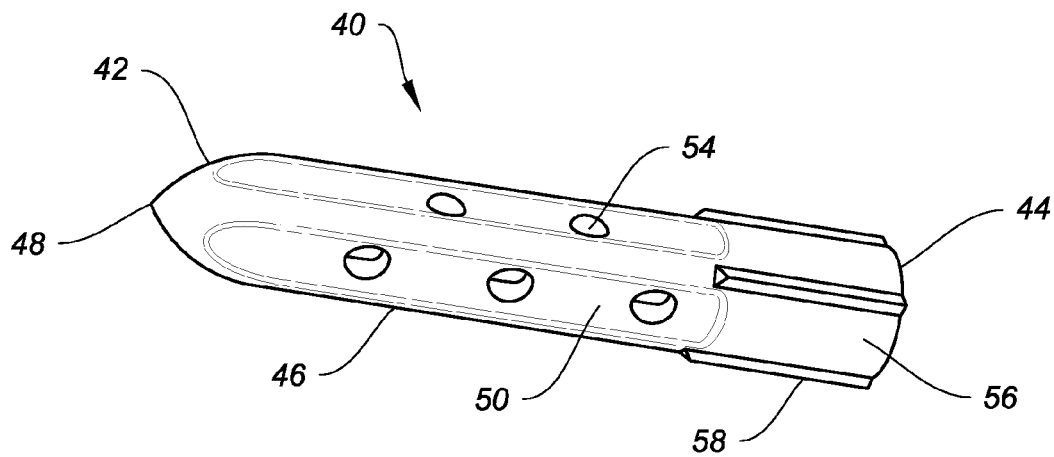
FIG. 2A illustrates perspective view of another exemplary embodiment of an implantable device of the present invention.
Figure 2B:
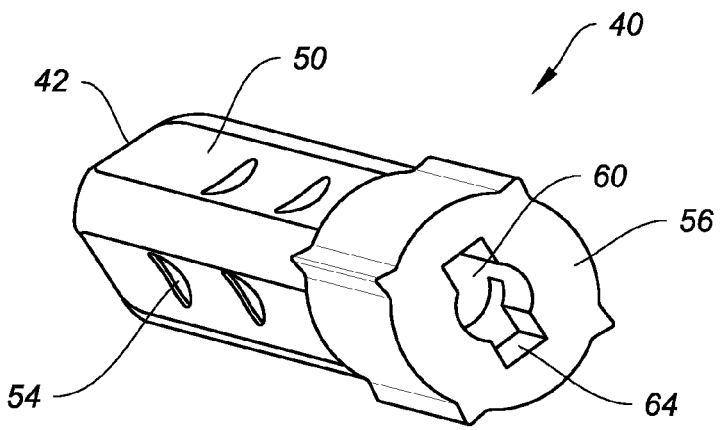
FIG. 2B illustrates a perspective rear view of the implantable device of FIG. 2A.
Figure 2C:
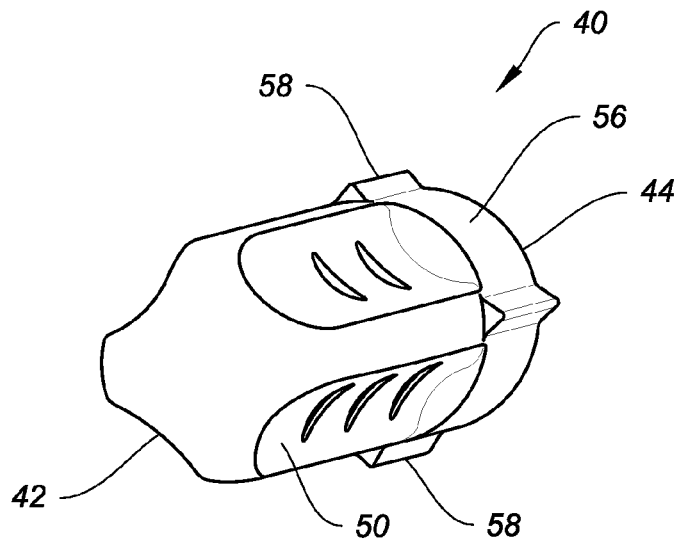
FIG. 2C illustrates a perspective front view of the implantable device of FIG. 2A.

FIGS. 2A-2C illustrate an implantable device 40 similar in many ways to implants 10 or 30, but with an additional surface feature for enhanced bone tissue engagement. Implant 40 may include a first, leading end 42 and a second, trailing end 44 extending between which is an elongate body 46. Like implant 10, implant 40 can further include a tapered nose 48, flutes 50 extending longitudinally along its body 46, a central canal 60, and one or more pores 54 in communication with the central canal 60. In addition, the implant 40 may include a collar or cap 56 at the second, trailing end 44. The cap 56 may include fins 58 extending around its diameter as shown, along with a slot 64 for receiving a tool, such as for example an insertion tool or an injection instrument (not shown).

The fins 58 enable the implant 40 to be inserted in a combination slip-fit, press-fit manner. The implant 40 may have primary stability with the press-fit connection of the fins 58 to the bone tissue, while the remaining surface of the implant 40 may be further stabilized after a cement is injected through the implant 40 and allowed to harden, as previously described. In addition, the cap 56 may also serve to prevent cement from escaping out of the bone tissue and away from the implant 40 during injection.

The fins 58 may have a uniform height across their length, or the fins 58 may have varying heights across their length to create a curved, wavy, or irregular pattern. For example, the fins 58 may be S-shaped, V or W-shaped to create a jagged spine-like profile. Further, instead of fins 58, it is contemplated that the surface feature on the cap 56 may also include structural elements such as threads, teeth, barbs, bumps, spikes, or other surface enhancements. These surface enhancements may serve as anti-migration features after implantation. In addition, a hydroxyapatite coating may also be applied to enhance incorporation into the surrounding bone tissue.

Figure 3A:
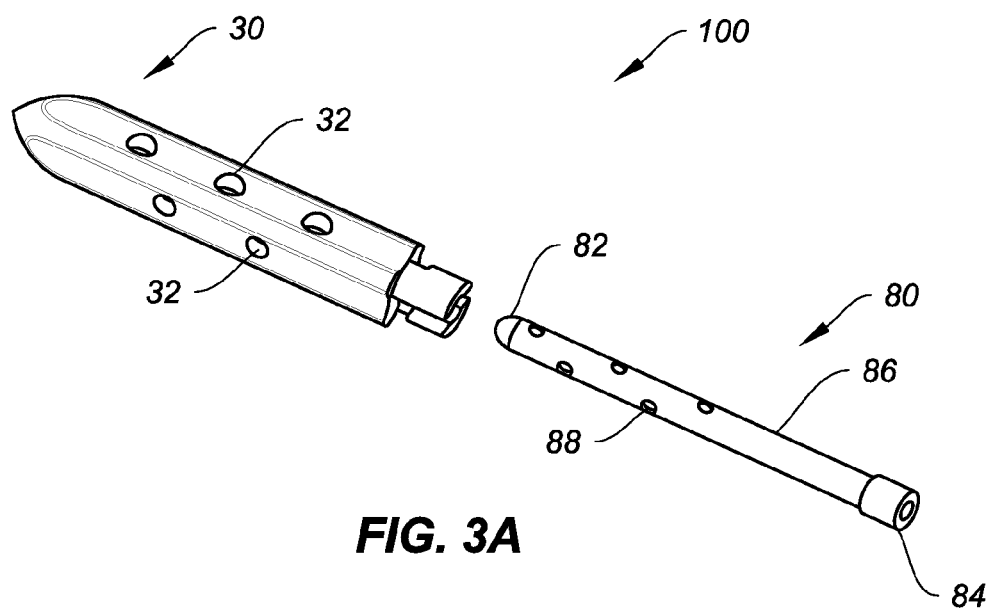
FIG. 3A is a perspective view of the implantable device of FIG. 1 along with an injection instrument.
Figure 3B:
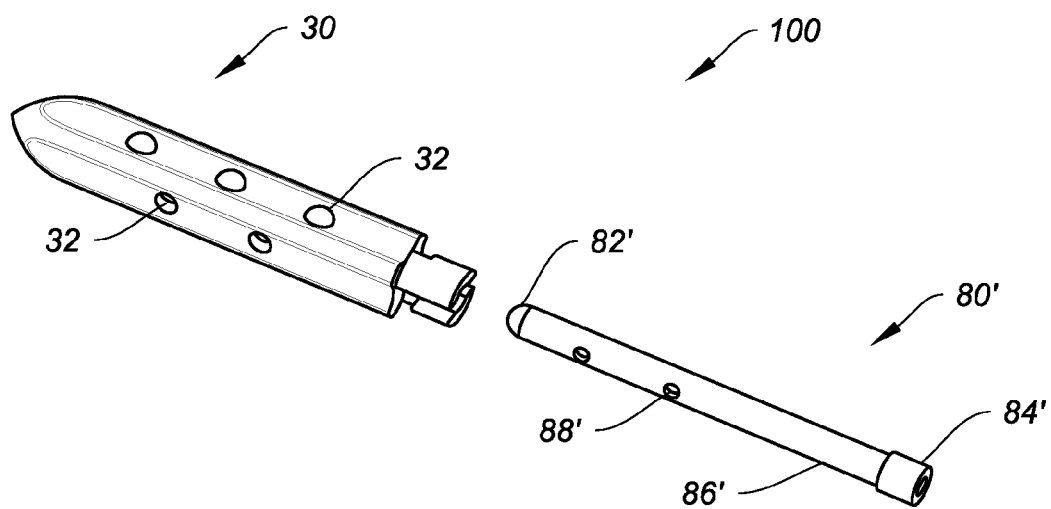
FIG. 3B is a perspective view of the implantable device of FIG. 1 along with another injection instrument.
Figure 3C:
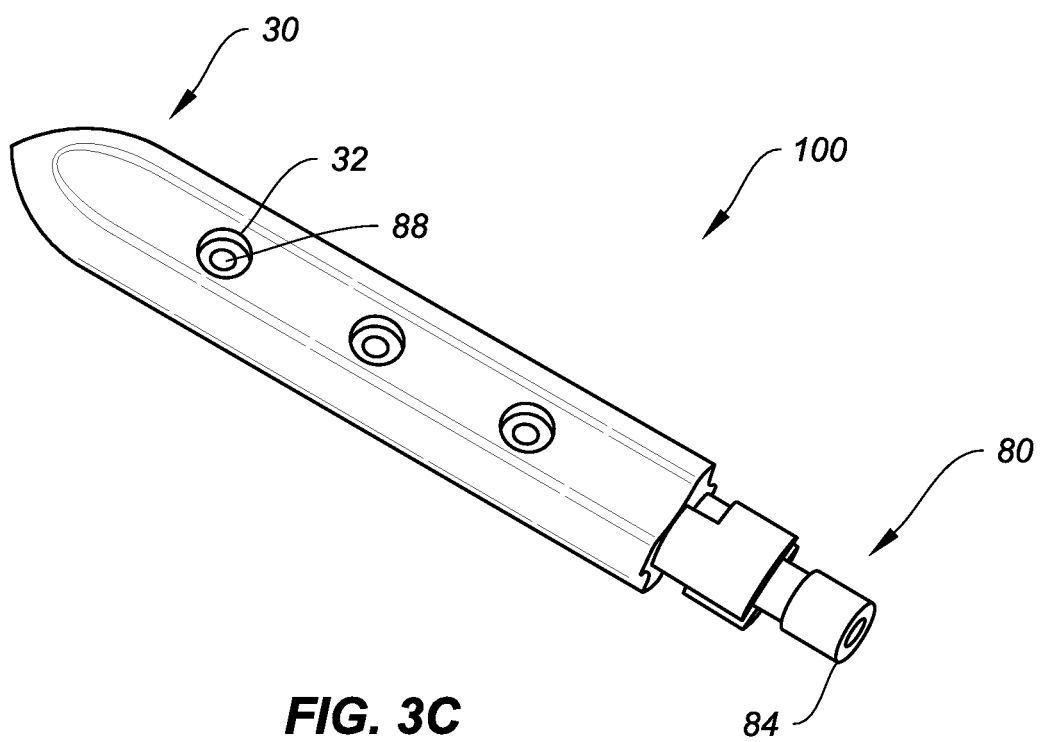
FIG. 3C illustrates the implantable device and injection instrument of FIG. 3A together.

FIGS. 3A-3C illustrate a system 100 for controlling the manner of injecting a bone cement or hardening material, or a bone augmentation material, into a bone defect. Turning to FIG. 3A, the system 100 may include an implantable device such as implant 30 (or implant 10) and an injection tool 80 configured for use with the implant 30. Injection tool 80 may have a first, leading end 82, a second, trailing end 84, a shaft 86 extending in between, and one or more pores 88 on the shaft 86. The injection tool 80 may be sized and configured to slide into the implant 30, as shown in FIG. 3C. When the pores 88 of the injection tool 80 do not match up with the pores 32 of the implant 30, no material can be extruded. But when extrusion is desired, the injection tool 80 may be adjusted or rotated such that its pores 88 align with the pores 32 on the implant 30 and thereby enable the injected material to be extruded out of the implant 30.

As shown in FIG. 3B, the injection tools 80, 80' may vary in the number of pores 88 provided as well as the orientation of the pores 88. In the present example shown, an injection tool 80' is similar in most respects to injection tool 80, except that less pores 88' are provided, and the pores 88' are located only at a select region of the tool 80'. To enable a user to selectively control the directionality of flow of the injectable material, the injection tool 80' may be utilized with implant 30. Material would only extrude where the pores 32 of the implant and the pores 88' of the injection tool 80' align.

FIGS. 4A-4E illustrate yet another exemplary embodiment of an implantable device 110 of the present invention that can be used in combination with an injectable material, if desired. Implant 110 may include a first, leading end 112 and a second, trailing end 114 extending between which is an elongate body 116. Implant 110 can further include a recessed portion 120, and one or more pores 124 residing within the recessed portion 120. The pores 124 may be in communication with a central canal 130 extending through the longitudinal axis of the implant 110. In addition, the implant 110 may include a flanged collar 134 at the second, trailing end 114. The flanged collar 134 may include a tool-engaging slot, such as a hexagonal slot 136.

In use, the recessed portion 120 of the implant 110, which includes the pores 124, enables the user to control the directionality of the flow of injectable material being extruded. The recessed portion 120 also serves to contain the area where the material resides. Additionally, the flanged collar 134 may serve to block extruded material from escaping out of the implantation site.

Figure 4A:
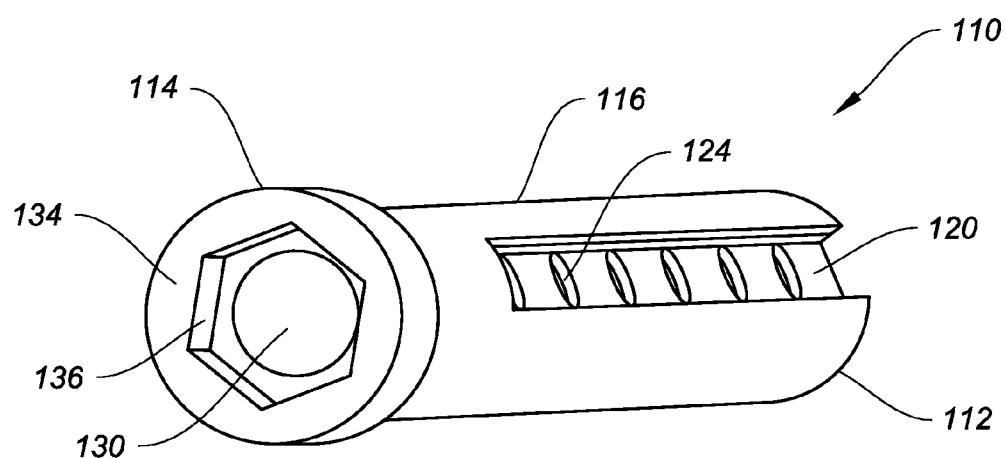
FIG. 4A is a perspective view of another exemplary embodiment of an implantable device of the present invention.
Figure 4B:
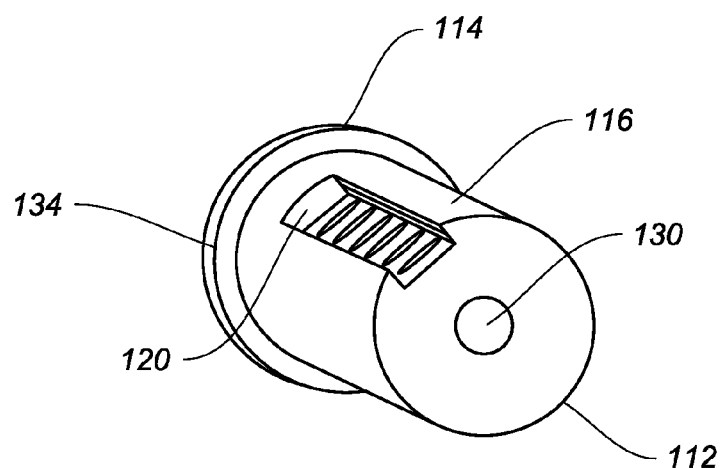
FIG. 4B is a perspective rear view of the implantable device of FIG. 4A.
Figure 4C:
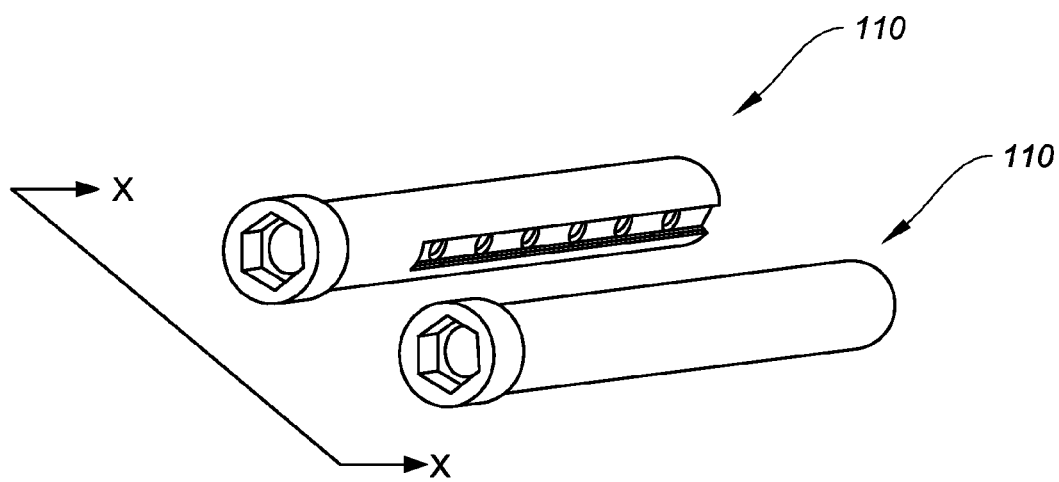
FIG. 4C shows a pair of implantable devices of FIG. 4A.
Figure 4D:
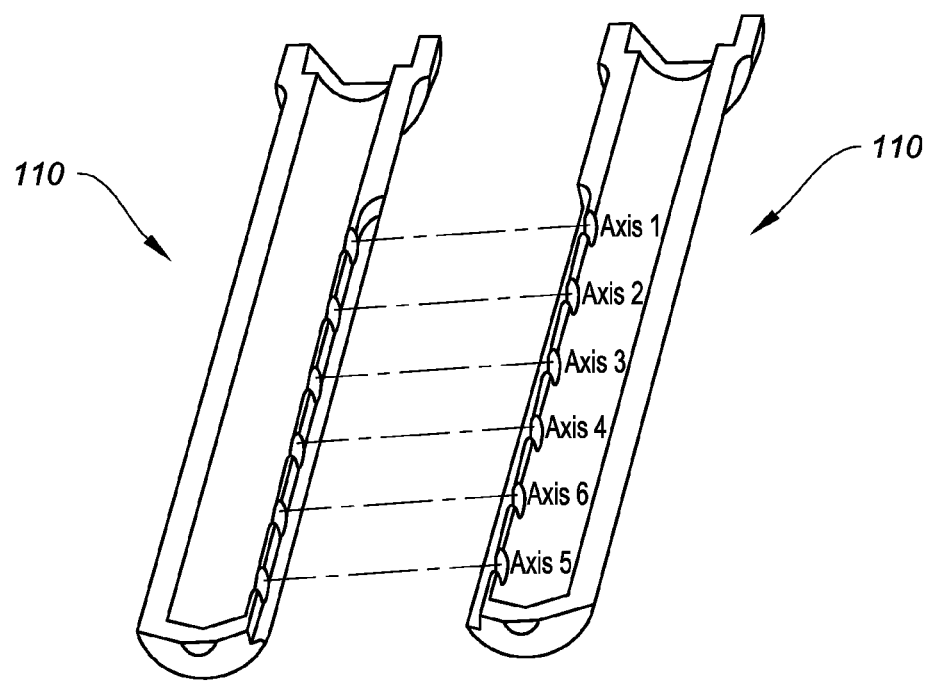
FIG. 4D shows a cross-sectional view of the implantable devices of FIG. 4C along lines X-X.
Figure 4E:
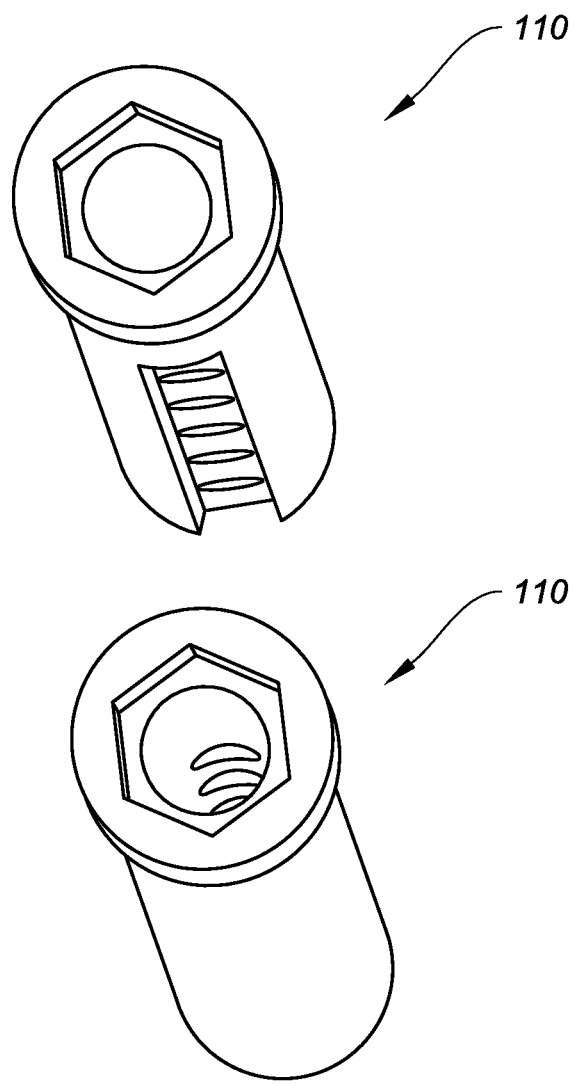
FIG. 4E shows another perspective view of the implantable devices of FIG. 4C.

FIGS. 4C-4E show one manner of using one or more implants 110 of the present invention. In one example, a pair of implants 110 may be used in combination with one another in a manner that allows communication between the implants 110. In some situations, it may be desirable to implant a pair of devices in parallel into the area of the bone defect to be treated. The devices may be arranged as shown in FIGS. 4C-4E, with the pores 124 facing one another. This configuration would enable the user with the ability to irrigate the site using one implant 110, and collect out of the other implant 110. For example, it is contemplated that one implant 110 may be closed to avoid leakage, while the other implant 110 opened to irrigate, in order to allow the user the ability to manipulate the directionality of materials being extruded from the opened implant 110. It would be possible, for instance, to inject a material into one implant, and allow the material to extrude out of the implant and into the pores 124 of the other implant if so desired. It is also possible to utilize multiple implants in this manner to stage, or space apart, the timing or introduction of material into the bone defect. For example, one material may be introduced earlier into an implant, while another material may be introduced at a later time into the other implant. The materials may be the same, or may be different. Of course, such a process is possible where the pores 124 of the implants 110 are aligned with one another, as shown in cross-section in FIG. 4D.

Figure 5A:
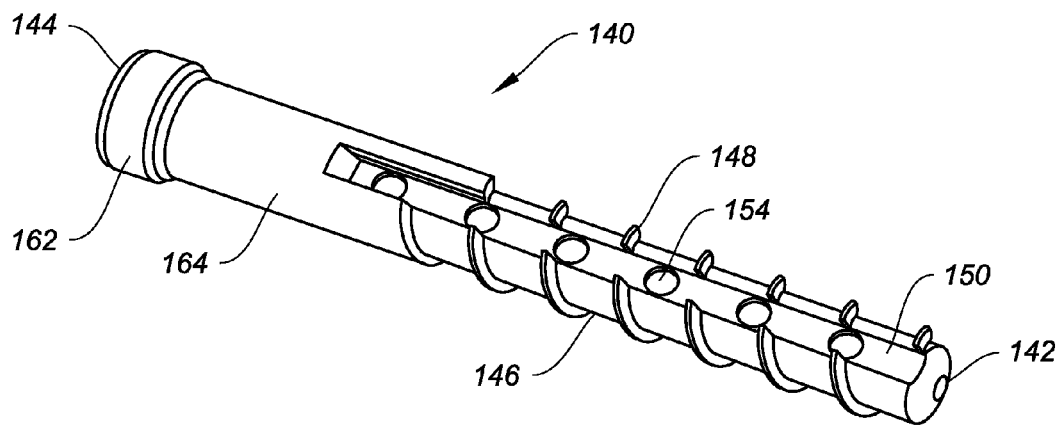
FIG. 5A illustrates a perspective view of another exemplary embodiment of an implantable device of the present invention.
Figure 5B:
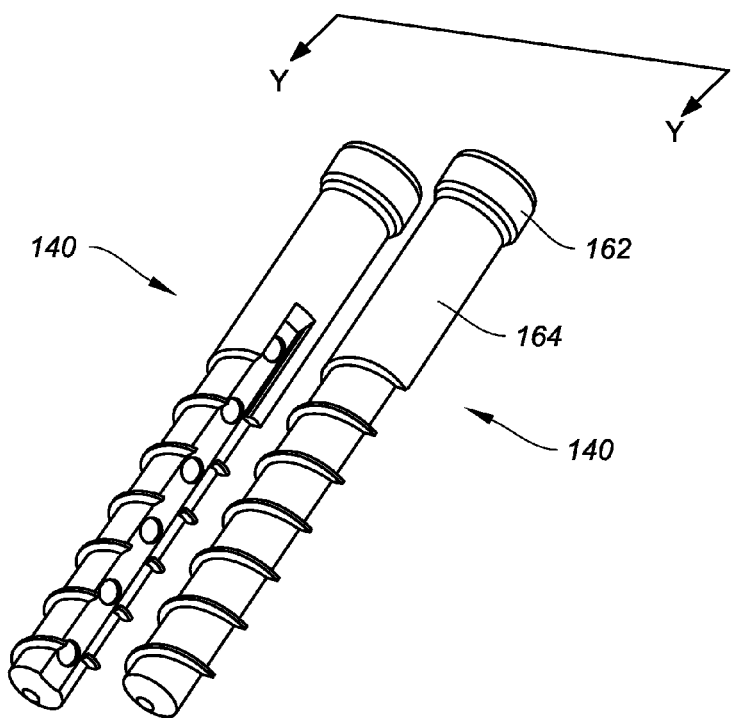
FIG. 5B illustrates a pair of implantable devices of FIG. 5A.
Figure 5C:
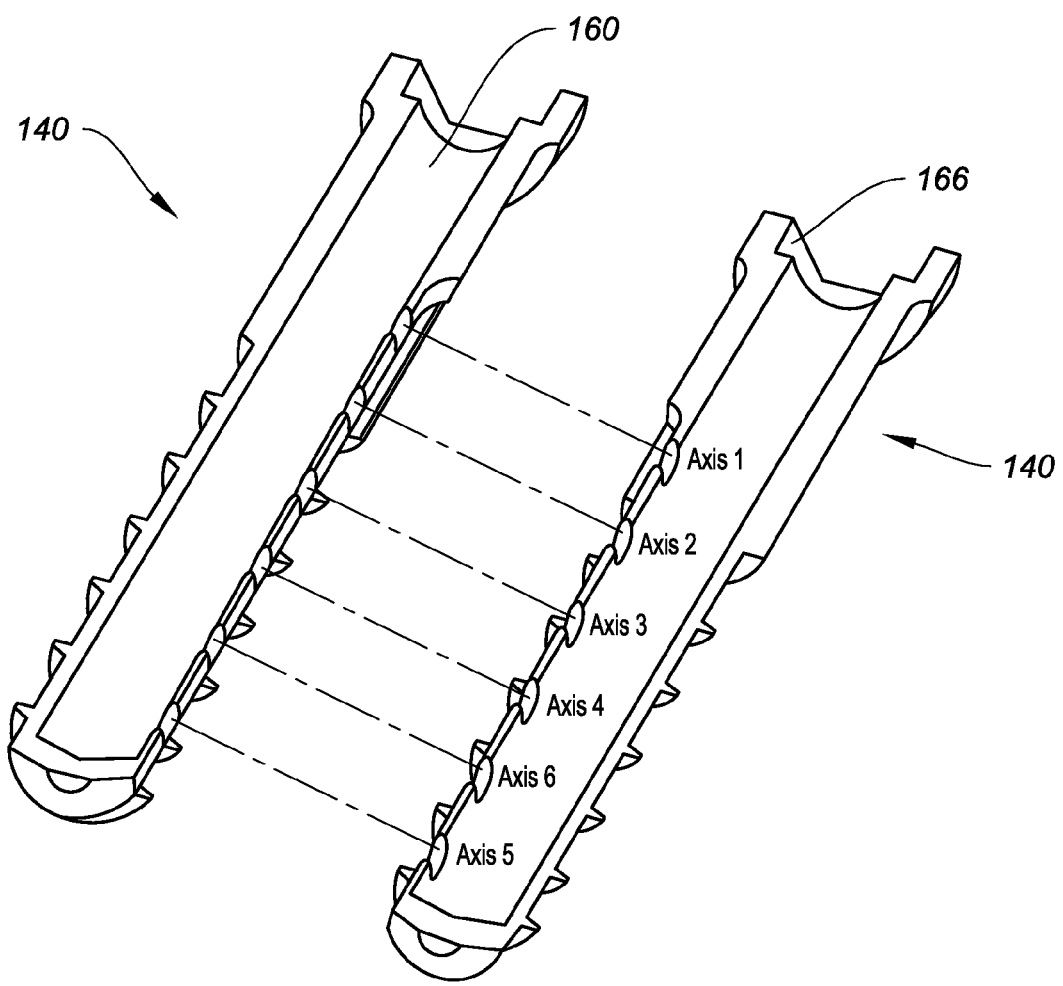
FIG. 5C shows a cross-sectional view of the implantable devices of FIG. 5B along lines Y-Y.

This same concept of multiple implant usage of implants in communication with one another may be employed with the threaded device 140 of FIGS. 5A-5C. Device 140 may include a first, leading end 142 and a second, trailing end 144 extending between which is an elongate body or shaft 146. A portion of the shaft 146 may include threads 148, as shown. Device 140 can further include a recessed portion 150, and one or more pores 154 residing within the recessed portion 150. The pores 154 may be in communication with a central canal 160 extending through the longitudinal axis of the device 140. In addition, the device 140 may include a cap 162 at its second, trailing end 144. The cap 162 may extend into a collar 164 extending partially down the shaft 146. As shown in FIG. 5C, the cap 162 may also include a tool-engaging slot 166 for receiving an insertion tool or an injection tool, for example.

By providing a device 140 with threads 148, it is possible that the device 140 be implanted and left inside the bone, or it can be removed from the bone by screwing the device 140 back out of the bone. In either scenario, the cap 162 as well as the collar 164 serve as shoulders or ramps to prevent any extruded material through the device 140 from backing out.

Figure 6A:
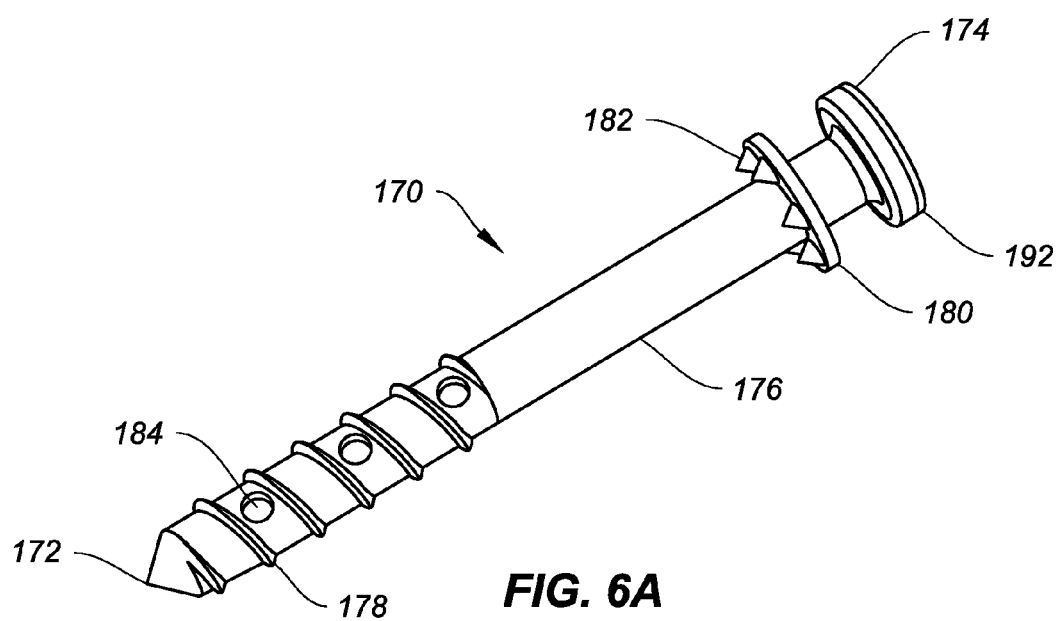
FIG. 6A illustrates a perspective view of another exemplary embodiment of an implantable device of the present invention.
Figure 6B:
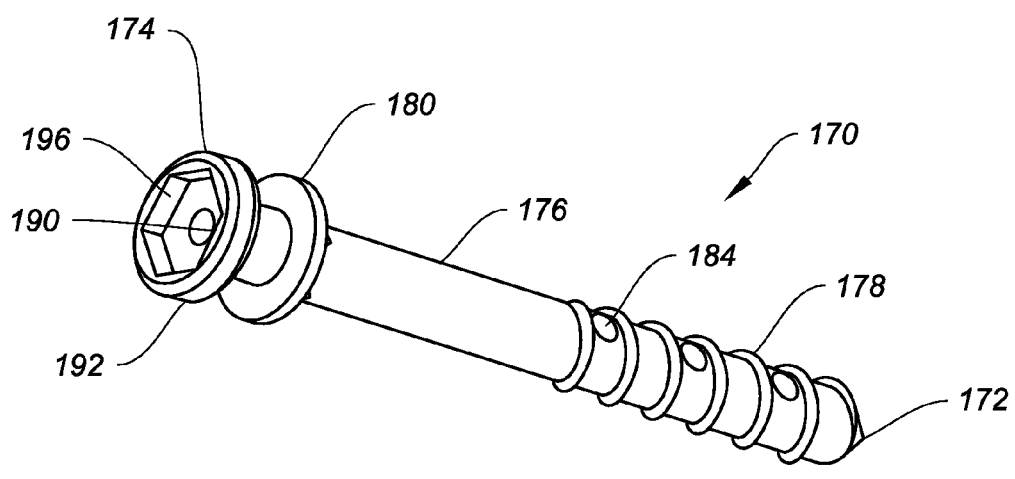
FIG. 6B illustrates another perspective view of the implantable device of FIG. 6A.

FIGS. 6A and 6B illustrate a device 170 of the present disclosure that is configured to allow cortical bone purchase or anchorage. The device 170 may include a first, leading end 172 and a second, trailing end 174 extending between which is an elongate shaft (or body) 176. A portion of the shaft 176 may include threads 178, as shown, while a central canal 190 extends through the shaft 176. Pores 184 are provided at the region with threads 178, and are in fluid communication with the central canal 190. The device 170 further includes a flange 180 with a surface feature on its underside for improved bone purchase. In the embodiment shown, the surface feature may include spikes (or teeth) 182, for example. A cap 192 is also provided with a tool-engaging slot 196 for receiving an insertion tool or an injection tool, for example.

Since the pores 184 are isolated at the threaded portion of the device 170, this particular embodiment allows the user better control of where the injectable material is extruded. Further, the spiked flange 180 allows the device 170 additional anchorage and stability, and is particularly useful where the device 170 is secured to the outer bone surface. Accordingly, it is possible to provide devices where a portion is inside bone and a portion remains outside the bone. In the present example, the cap 192 of the device 170 may sit proud outside of the bone surface, although it is contemplated that the device 170 could be easily configured so that the cap 192 has an overall low profile outside of the bone.

FIGS. 7A-7F represent a system 200 and method of using the system 200 to inject a bone cement or other hardening material, or a bone augmentation material such as a biologic agent, into a bone defect. The system 200 comprises a threaded device 210 similar to the threaded devices 140, 170 already described above. However, threaded device 210 may include threads 218 along its entire length, and act as a drill bit. The threaded device 210 may include a first, leading end 212 and a second, trailing end 214 extending between which is an elongate shaft (or body) 216 having threads 218 extending along its length. Pores 224 may be provided in between the threads 218, as shown, though it is contemplated that the pores 224 may also be provided on the threads 218, if desired.

System 200 further includes an insertion tool 240 configured for use with the threaded device 210. The tool 240 may include a first, device-attachment end 242 that may provide a quick release connection with the device 210. For example, the device-attachment end 242 may be a threaded end. The insertion tool 240 also includes an elongate shaft (or body) 246 extending from the device-attachment end 242 into a second, opposed end 244. The second end 244 may be configured with a contoured handle 248. The contoured handle 248 may include an opening 250 with an injection port 252 that extends through the length of the tool 240 and is in communication with a central canal (not shown) running down the length of the threaded device 210.

Also provided with system 200 is a protection sleeve 270 configured for use with the threaded device 210 and the insertion tool 240. The protection sleeve 270 may include a rounded or smooth bone-contacting end 272 and a device insertion end 274 at an opposite end. A tubular body 276 may extend in between the first and second ends 272, 274. The tubular body 276 may include a threaded channel 278 that matches the female threads 218 of the threaded device 210. A handle 280 may be provided on the tubular body 276.

Figure 7A:
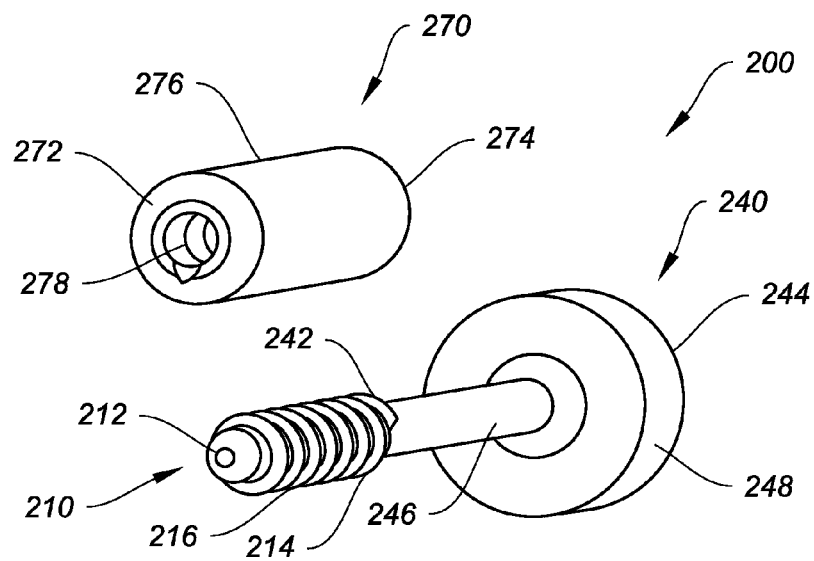
FIG. 7A illustrates an exemplary embodiment of an injection system of the present invention.
Figure 7B:
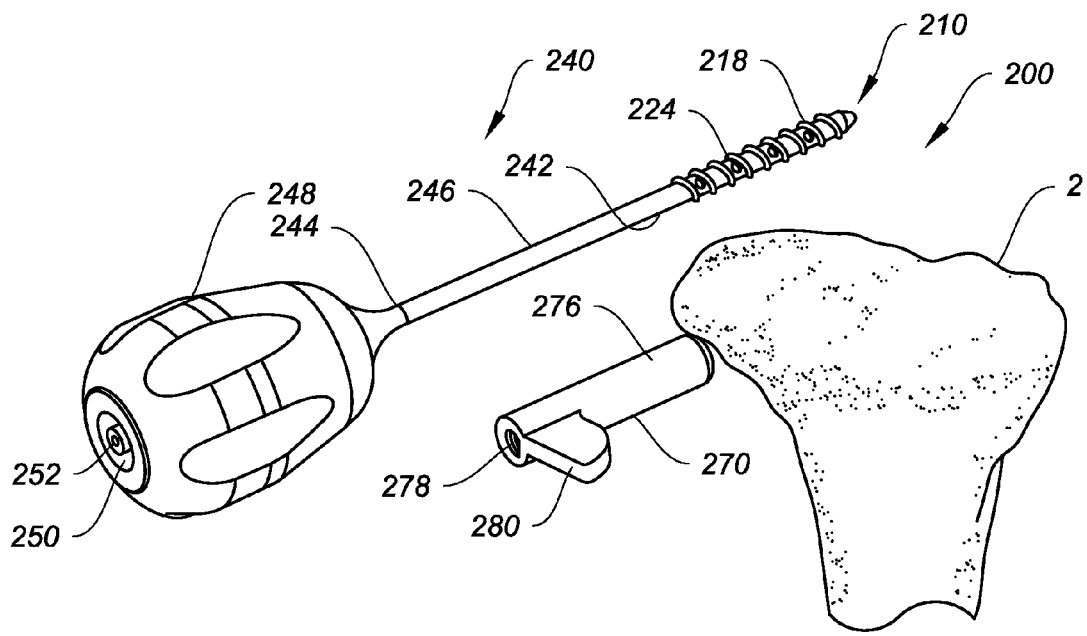
FIGS. 7B-7F illustrate a method of using the injection system of FIG. 7A.

In use, the threaded device 210 may be attached to the insertion tool 240, as shown in FIG. 7A. Then, the protection sleeve 270 may be placed with the first, bone-contacting end 272 against the bone 2 to be treated, as shown in FIG. 7B. The bone-contacting end 272 may be either round and/or smooth, or it may be roughened for better bone contact, if desired. While holding the protection sleeve 270 firmly against the bone 2 using handle 280, the threaded device 210 may be threaded into the protection sleeve 270 and into the bone 2, which may or may not already have a bone cavity pre-drilled to receive the threaded device 210. Once the threaded device 210 is inside the bone 2 (see FIG. 7F), an injection tool (not shown) may be attached to the injection port 252 at the handle 248 of the insertion tool 240. The desired injectable material may then be injected through the insertion tool 240, into the threaded device 210, and allowed to extrude out of one or more pores 224 of the threaded device 210 into the bone 2.

Figure 7C:
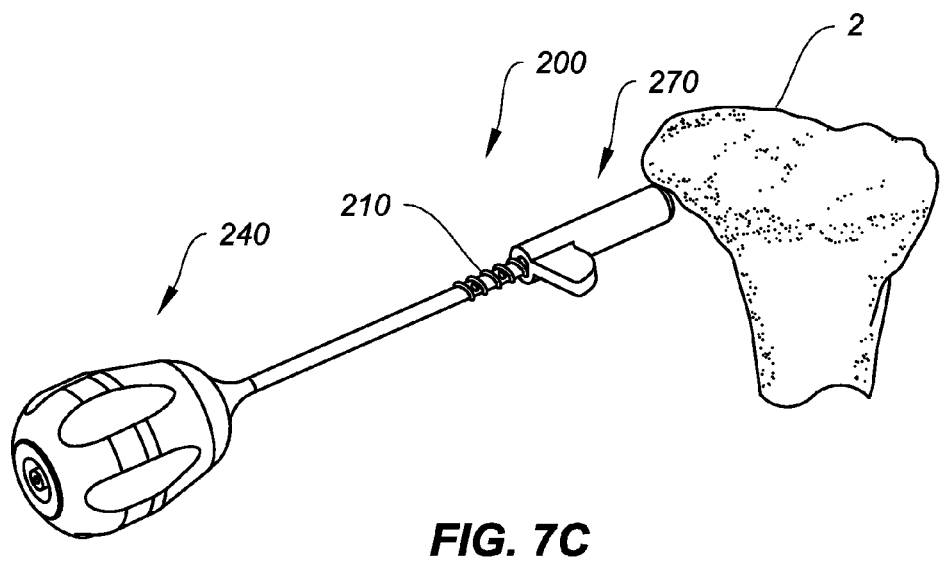
Figure 7D:
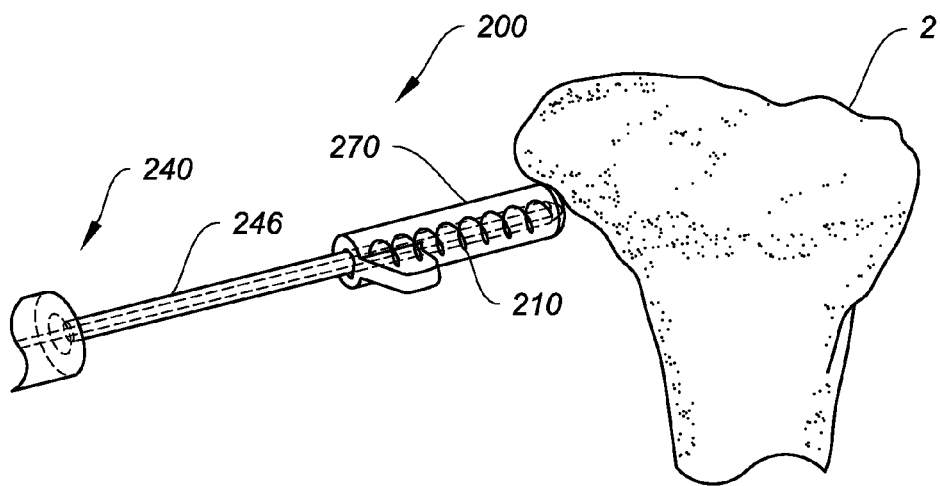
Figure 7E:
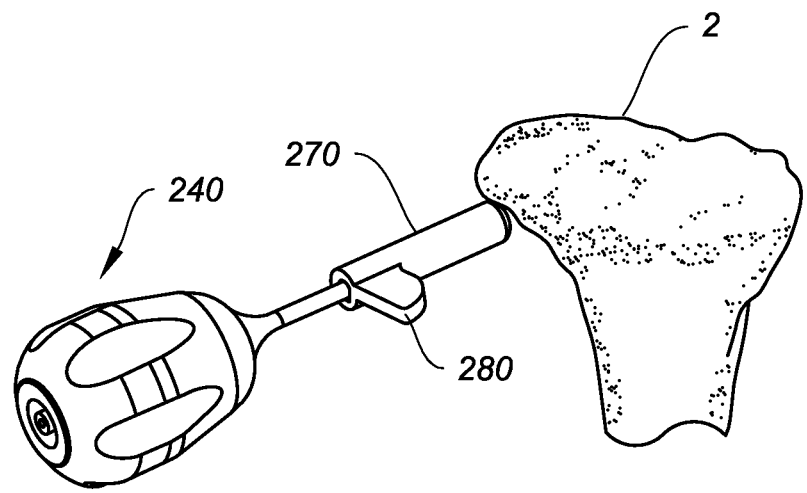
Figure 7F:
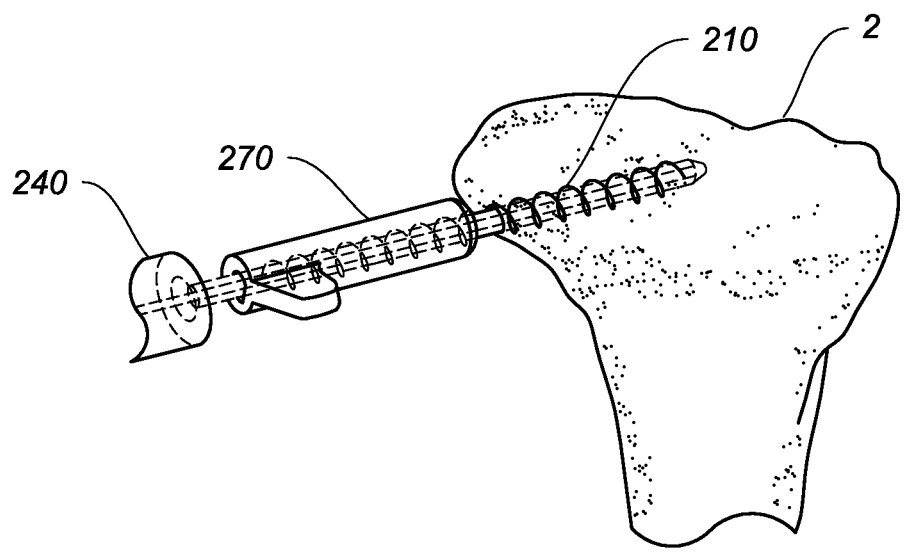

In one method of using the system 200 of the present disclosure, one or more threaded devices 210 may be employed in the bone 2 to be treated. A quantity of injectable material, such as a bone cement, can be injected and allowed to extrude into the bone 2. After some period of time sufficient to allow the cement to harden, the threaded device(s) 210 may be retracted by unscrewing it/them out of the protection sleeve 270. Material may be injected again, allowed to harden, and the threaded device 210 retracted. These steps may be repeated until sufficient cement has been extruded and hardened, whereupon the threaded device(s) 210 may be removed from the bone 2 entirely in stages, as shown in FIGS. 7C-7E. The protection sleeve 270 prevents cement from backing out, or extruding out of the bone 2 during the entire process, as the user holds the sleeve 270 firmly against the bone 2 throughout the procedure.

System 200 provides the user with a plurality of working channels for injecting a cement or other injectable material into a bone 2 to be treated. These working channels may be coaxial, as shown, and enable the user to inject some or all of the material at once, or in a staged fashion to control the injection process. In an example where an open ended device is employed, cement may be injected at the open end only and allowed to harden so as to close off the open end. Subsequently, additional cement or other material may be injected through the rest of the device so that the material extrudes out through provided pores or channels and not through the open end. In addition, system 200 may be used with any of the threaded devices disclosed herein, allowing the devices to serve as a drill bit as well as an injection tool.

Figure 8A:
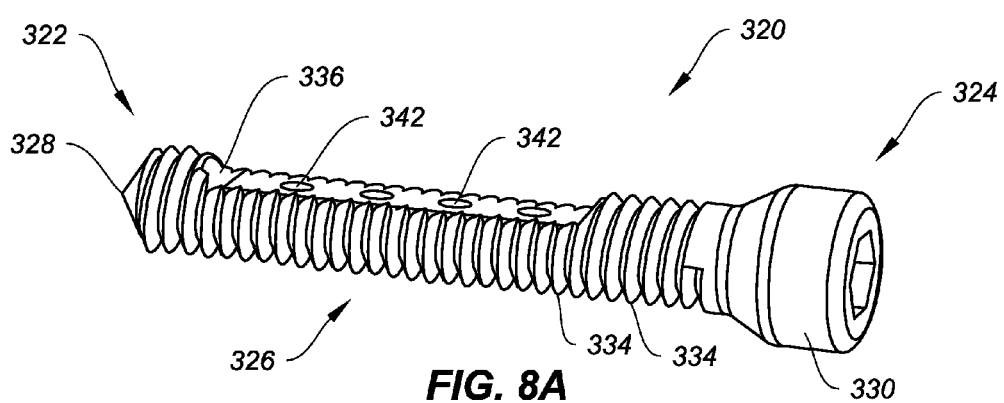
FIG. 8A is a perspective view of an exemplary embodiment of an implantable device of the present invention.
Figure 8B:
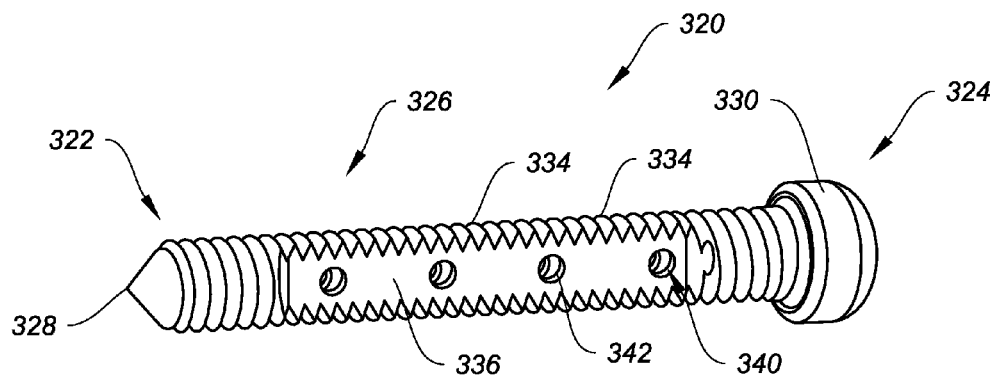
FIG. 8B is another perspective view of the implantable device of FIG. 8A.

FIGS. 8A and 8B illustrate yet another exemplary embodiment of an implantable device of the present disclosure. Implant 320 can include an elongate body or shaft 326 extending between a first, leading end 322 and a second, trailing end 324. Elongate body 326 may be provided with external threads 334 extending along its length. The first end 322 of the implant 320 can include a tapered nose or tip 328 to facilitate ease of insertion to the target site. If so desired, the tip 328 may also be rounded. The implant 320 may be configured to be self-tapping, self-drilling, or the implant 320 may be configured for insertion after the creation of a pre-drilled hole in the bone being treated.

The second end 324 may include a head region 330 having a tool-engaging opening 332 for receiving an insertion tool (not shown). This tool-engaging opening 332 may also extend into a central channel 340 that stretches down the length of the implant 320 a predetermined distance, such as for example, half-way down its length, three-quarters down its length, etc. As shown, the elongate body 326 may have a cutaway portion 336 that creates a flattened, depressed surface on the elongate body 26. One or more side ports 342 may be provided on the cutaway portion 336, with each side port 342 being in communication with the central channel 340. The side ports 342 enable the user to introduce a flowable material, such as a bone cement or augmentation material as previously described, into the central channel 340 and allow the material to extrude out of the side ports 342 and away from the elongate body 326.

Although shown with a plurality of side ports 342, each being similar in size, it is understood that the dimensions of the side port 342 may vary. For example, it is contemplated that the side ports 342 may have incremental sizes along the length of the elongate body 326. Also, the side ports 342 may have a predetermined geometric pattern, such as for example, a staggered arrangement, instead of being coaxial.

Figure 9A:
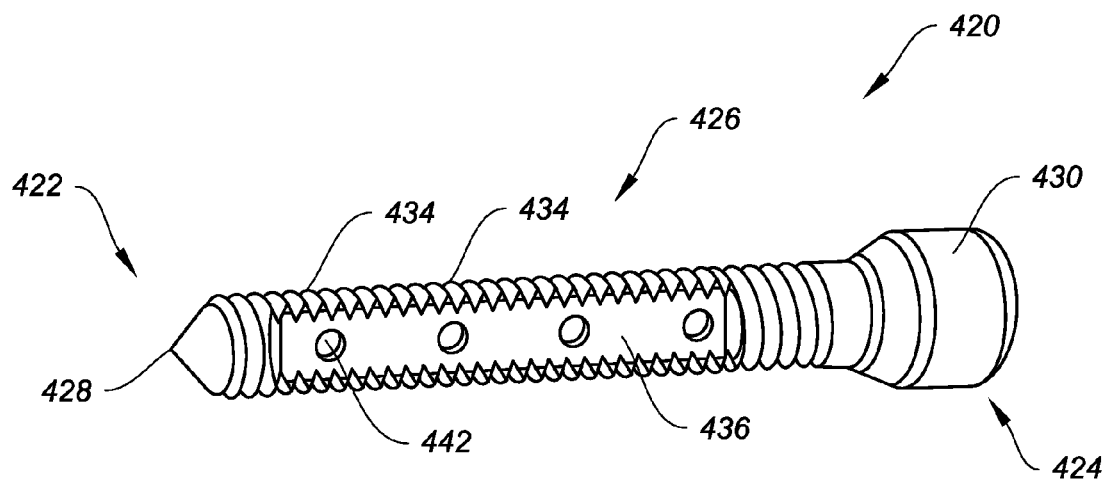
FIG. 9A is a perspective view of another exemplary embodiment of an implantable device of the present invention.
Figure 9B:
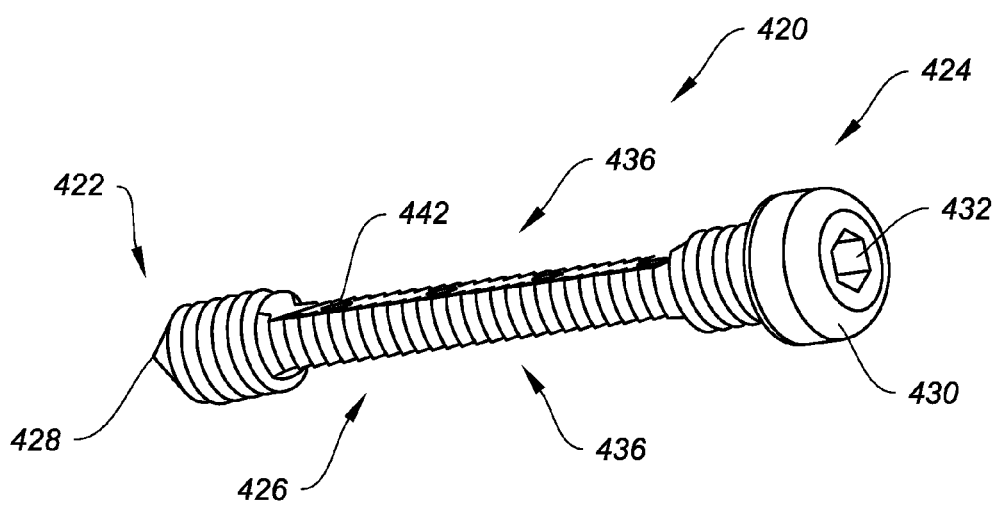
FIG. 9B is another perspective view of the implantable device of FIG. 9A.

FIGS. 9A and 9B illustrate another exemplary embodiment of an implantable device of the present disclosure. Implant 420 is similar to implant 320 previously described. Like implant 320, implant 420 may also include an elongate body 426 extending between a first, leading end 422 and a second, trailing end 424. Elongate body 426 may be provided with external threads 434 extending along its length. The first end 422 of the implant 420 can include a tapered nose or tip 428 to facilitate ease of insertion to the target site, while the second end 424 may include a head region 430 having a tool-engaging opening 432 for receiving an insertion tool (not shown). This tool-engaging opening 432 may also extend into a central channel 440 that stretches down the length of the implant 420 a desired distance.

As FIG. 9B shows, the elongate body 426 may have a pair of cutaway portions 436, creating flattened, depressed surfaces on opposed lateral sides of the elongate body 426. Each cutaway portion 436 may include one or more side ports 442, with each side port 442 being in communication with the central channel 440 to enable the user to introduce a flowable material, such as a bone cement or augmentation material as previously described, into the central channel 440 and allow the material to extrude out of the side ports 442 and away from the elongate body 426.

FIGS. 10 and 11A-11C illustrate one exemplary method of use in which the implant 420 may be used to treat a bone defect in a bone 2 of a joint. As shown in partial cross-section in FIGS. 10 and 11A-11C, the bone defect may be a bone marrow lesion 6 at the subchondral level below the articular surface 4 of a tibia of a knee joint. The implant 420 may be positioned in the tibia bone 2 below the bone marrow lesion 6 such that the external threads 434 on the elongate body 426 faces toward the lesion 6, as further shown in partial cross-section in FIG. 11B. This arrangement allows greater surface area contact between the lesion 6 and the implant 420, thereby providing more mechanical strength and structural integrity to the area to be treated, than if the implant 420 was rotated 90 degrees, for instance, where one of the cutaway portions 436 faced the bone marrow lesion 6.

Once the implant 420 is properly positioned relative to the defect or lesion 6, a flowable material 70 may be introduced into the central channel 440 of the implant 420 and extruded out through the side ports 442. The flowable material 70, which may be a hardening or augmentation material such as a bone cement (e.g., PMMA or CaP cement) or a bioactive agent (e.g, an osteoconductive, osteoinductive and/or osteogenic agent like a bone graft material), may be allowed to extrude away from the elongate body 426 and into the tissue of bone 2 surrounding the bone marrow lesion 6, as shown in partial cross-section in FIG. 11C. Accordingly, the implant 420 facilitates the dispersal of hardening or augmentation material in the area adjacent the bone marrow lesion 8 to further increase mechanical stability and/or enhance biological activity in order to treat or repair the structural makeup of the bone 2 in that region.

Figure 12A:
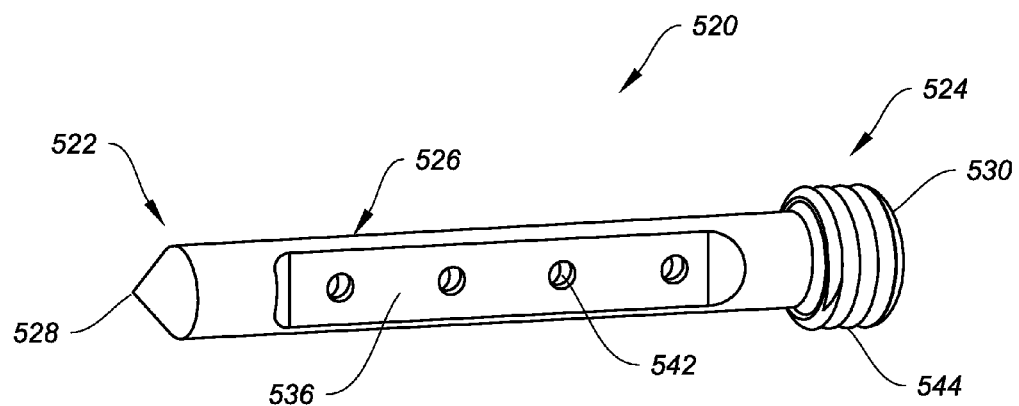
FIG. 12A is a perspective view of yet another exemplary embodiment of an implantable device of the present invention.
Figure 12B:
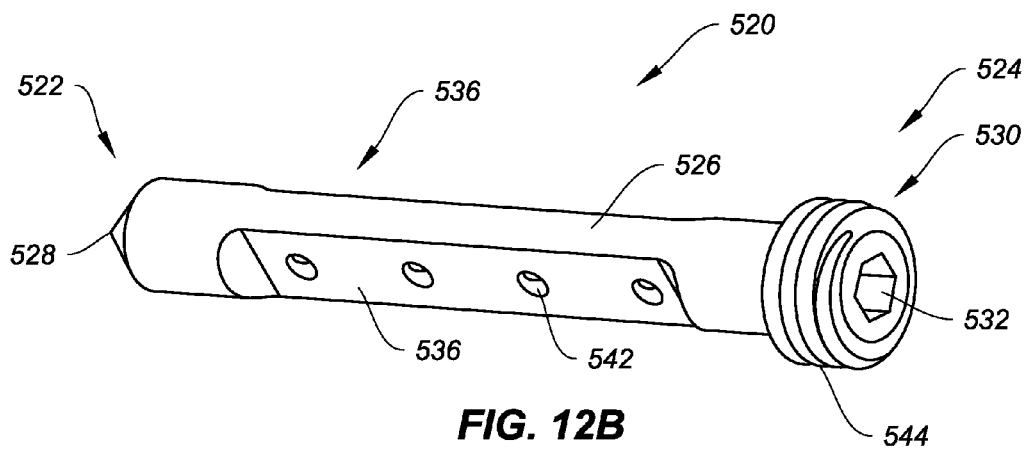
FIG. 12B is another perspective view of the implantable device of FIG. 12A.

FIGS. 12A and 12B illustrate yet another exemplary embodiment of an implantable device of the present disclosure. Implant 520 is similar to implant 320 previously described. Like implant 320, implant 520 may also include an elongate body 526 extending between a first, leading end 522 and a second, trailing end 524. The first end 522 of the implant 520 can include a tapered nose or tip 528 to facilitate ease of insertion to the target site, while the second end 524 may include a head region 530 having a tool-engaging opening 532 for receiving an insertion tool (not shown). This tool-engaging opening 532 may also extend into a central channel that stretches down the length of the implant 520 a desired distance.

Like implant 420, implant 520 may have a pair of cutaway portions 536, creating flattened, depressed surfaces on opposed lateral sides of the elongate body 526. Each cutaway portion 536 may include one or more side ports 542, with each side port 542 being in communication with the central channel to enable the user to introduce a flowable material, such as a bone cement or augmentation material as previously described, into the central channel and allow the material to extrude out of the side ports 542 and away from the elongate body 526.

However, unlike implant 320, implant 520 may be provided without any external threads, such that the implant 520 may be configured for press-fit engagement with bone tissue. The head region 530 of the implant 520 may have threads 544 to secure the implant 520 in place once properly positioned relative to the bone defect. These threads 544 may allow the head region to be secured to the cortical wall of the bone 2 (or tibia, in the case of a knee joint) near the lesion 6, which is stronger bone. Further, the threads 544 may act to help seal the head region 530 of the implant 520 into the bone opening to prevent extrusion of the flowable material or back-out of the implant 520. It is contemplated that any of the implants described and shown herein may be provided with a head region having such external threads for the reasons just mentioned.

Figure 13A:
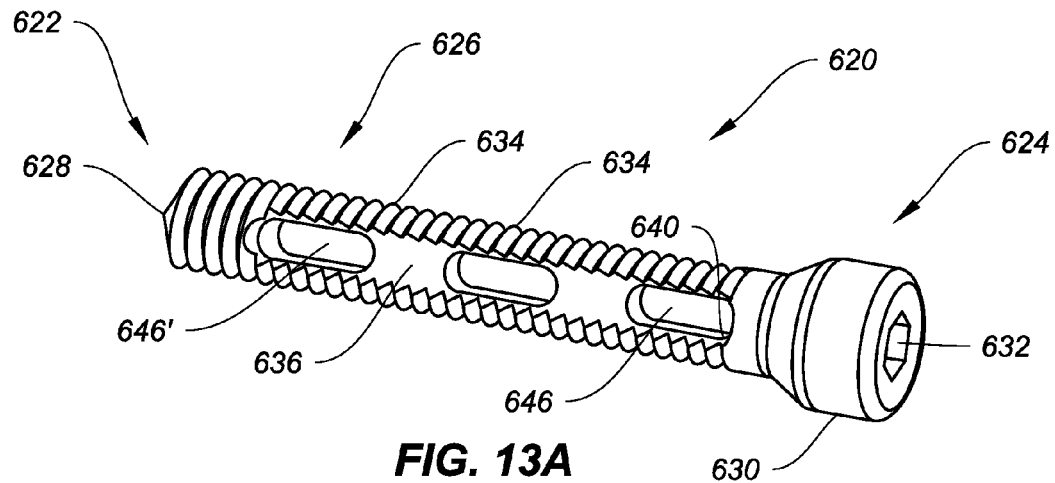
FIG. 13A is a perspective view of yet another exemplary embodiment of an implantable device of the present invention.
Figure 13B:
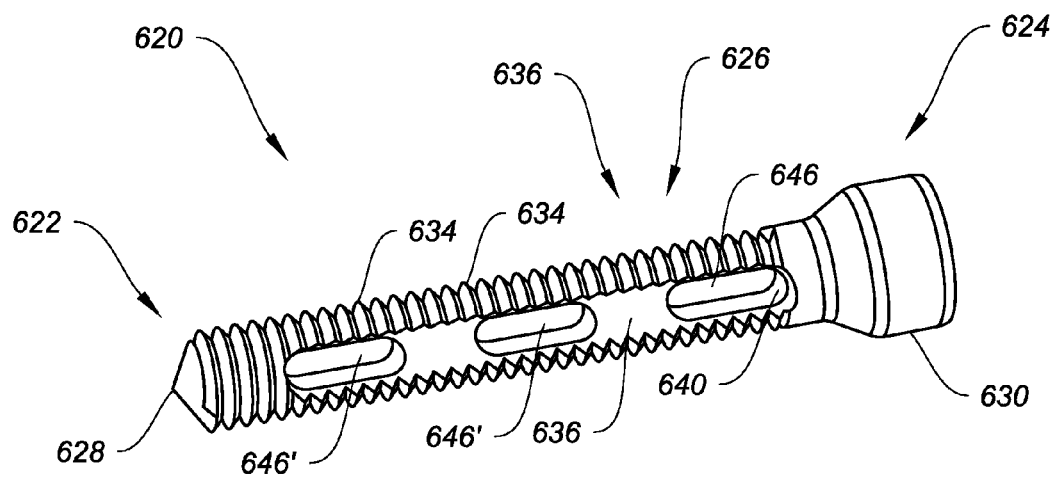
FIG. 13B is another perspective view of the implantable device of FIG. 12A.

FIGS. 13A and 13B shown still another exemplary embodiment of an implantable device of the present disclosure. Implant 620 is similar to implant 320 previously described. Like implant 320, implant 620 may include an elongate body 626 extending between a first, leading end 622 and a second, trailing end 624. Elongate body 626 may be provided with external threads 634 extending along its length. The first end 622 of the implant 620 can include a tapered nose or tip 628 to facilitate ease of insertion to the target site, while the second end 624 may include a head region 630 having a tool-engaging opening 632 for receiving an insertion tool (not shown). This tool-engaging opening 632 may also extend into a central channel 640 that stretches down the length of the implant 620 a desired distance.

Like implants 420 and 520, implant 620 may have a pair of cutaway portions 636, creating flattened, depressed surfaces on opposed lateral sides of the elongate body 626. A primary slot 646 may extend between the flattened surfaces of the cutaway portions 636, as shown. The primary slot 646 may be configured to be open and communicate with the central channel 640 to allow extrusion of a flowable material from the central channel 640 into the slot 646 and outside the elongate body 626. One or more additional, or secondary slots 646', may also be provided. These secondary slots 646' extend between the cutaway portions 636 similar to primary slot 646. However, the secondary slots 646' are not in communication with the central channel 640.

Figure 10:
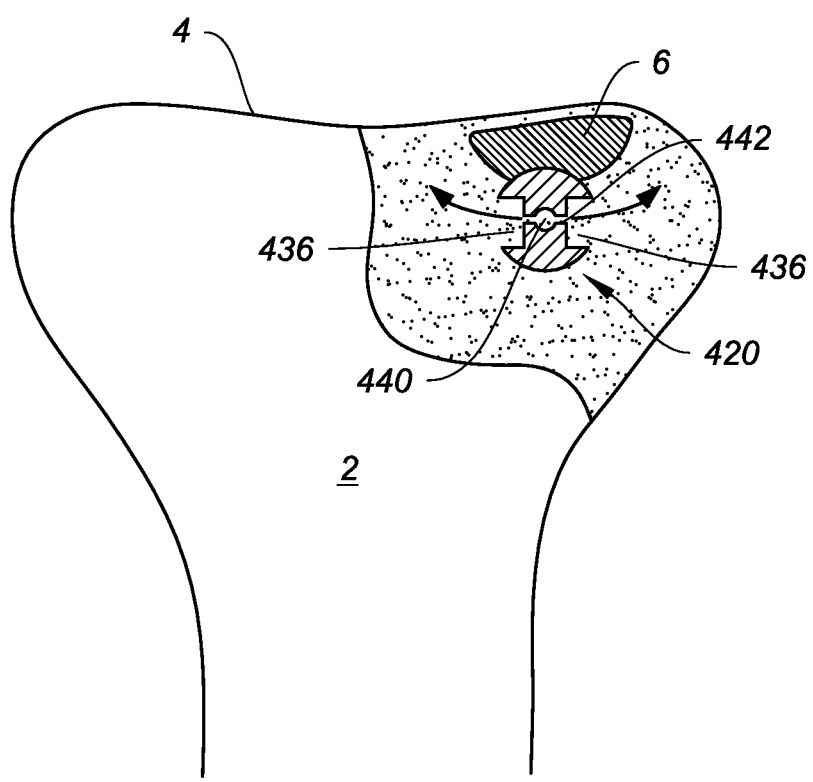
FIG. 10 is a partial cross-sectional view of the implantable device of FIGS. 9A and 9B in situ.
Figure 11A:
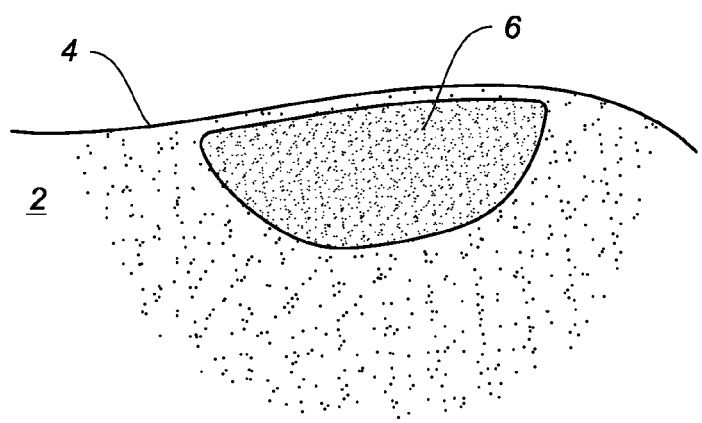
FIGS. 11A-11C illustrate a method of using the implantable device of FIG. 7.
Figure 11B:
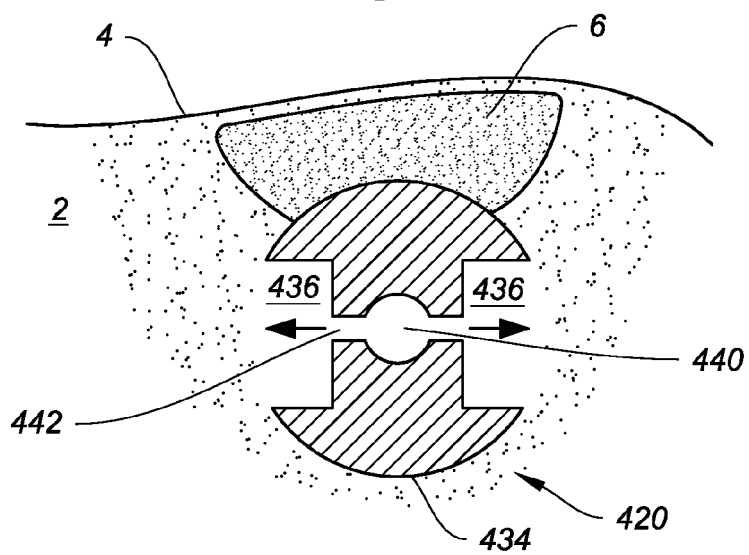
Figure 11C:
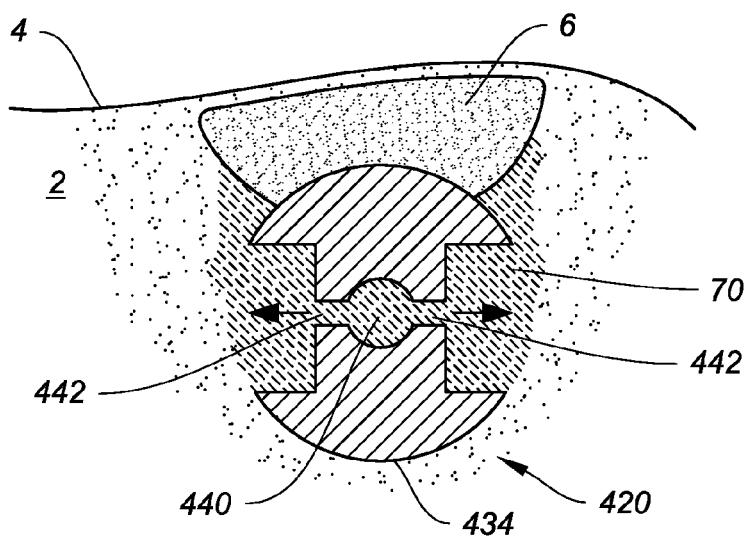
Figure 14:
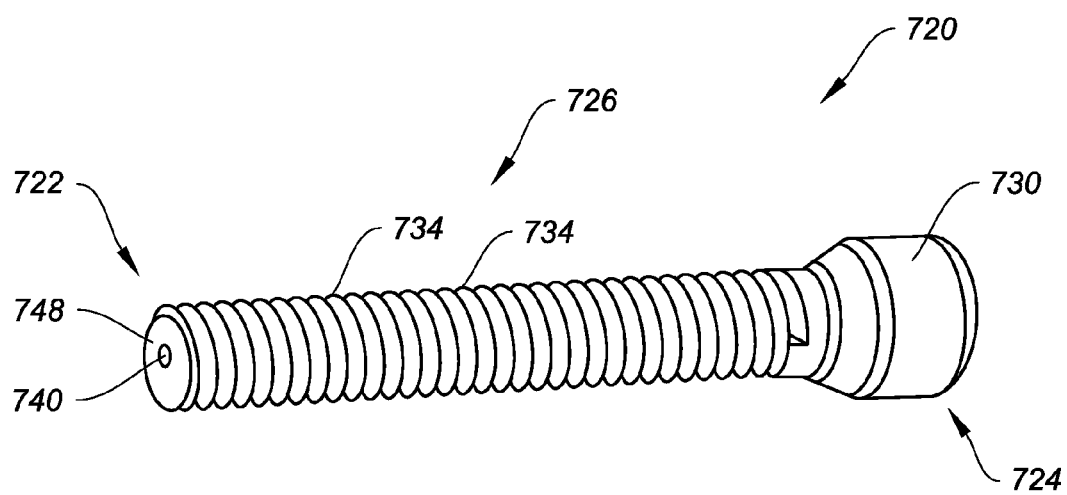
FIG. 14 is a perspective view of still another exemplary embodiment of an implantable device of the present invention.

In one exemplary method of treating a bone defect using implant 620, the implant 620 may be positioned below the bone defect such that the external threads 634 on the elongate body 626 faces toward the defect, similar to the arrangement shown in FIG. 10 and FIG. 11B. As described earlier, this arrangement allows the greatest surface area contact between the defect and the implant 620, thereby providing better mechanical strength and structural integrity to the area to be treated. After proper placement of the implant 620 relative to the defect, a flowable material may be introduced into the central channel 640 of the implant 620 and allowed to extrude into the primary slot 646. Further extrusion may be allowed such that the material flows out of the primary slot 646 and into one or more secondary slots 646' provided with the implant 620. It is contemplated that the open slots 646, 646' allow for easier transmission of cement and/or bone material from one side of the implant 620 to the other near the area of the lesion 6. The open slots 646, 646' could also allow for bony ingrowth into the implant 620 to further secure the implant to the bone FIG. 14 illustrates yet another exemplary embodiment of an implantable device of the present disclosure. Implant 720 shares similar characteristics to implant 320 previously described. Implant 720 may include an elongate body 726 extending between a first, leading end 722 and a second, trailing end 724. Elongate body 726 may be provided with external threads 734 extending along its length, and may be cannulated for use with a guide wire 90. As shown, the central channel 740 may be dimensioned to allow a K-wire 90, guide wire, or other equivalent insertion pin to pass through.

Unlike implant 20, however, the first end 722 of the implant 720 terminates at flat end surface 748. The second end 724 may include a head region 730 having an insertion tool-engaging opening similar to those previously described and shown. Also, as shown, the elongate body 726 is substantially cylindrical, with no cutaway portions thereabout.

Figure 15A:
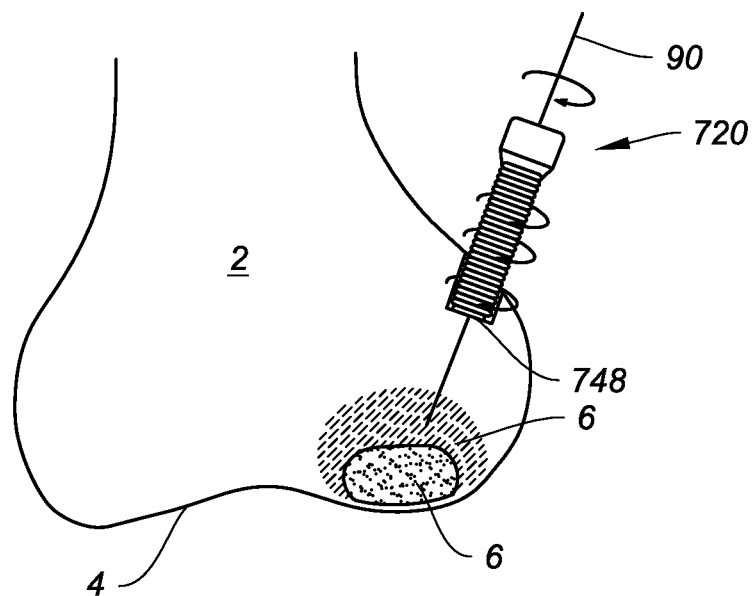
FIGS. 15A and 15B illustrate a method of using the implantable device of FIG. 14.
Figure 15B:
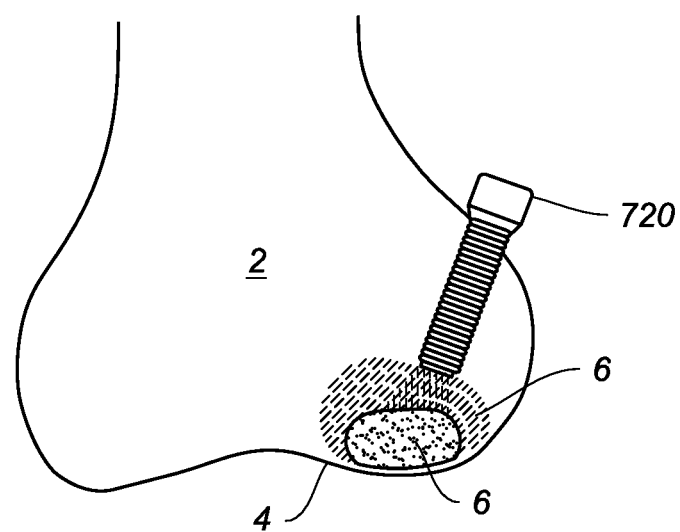

FIGS. 15A and 15B illustrate one exemplary method of treating a bone defect using implant 720. In the illustrated example, the bone 2 may be a femur of a knee joint, and the bone defect may be a bone marrow lesion 6 in the subchondral level below the articular surface 4 of a femur. A pre-drilled hole may be created to facilitate insertion of the implant 720, as shown in FIG. 15A. As the implant 720 is advanced towards the bone marrow lesion 6, tissue of bone 2 surrounding the defect becomes compacted against the lesion 6, as shown in FIG. 15B. It has been discovered that the bone tissue 2 surrounding a bone marrow lesion 6 tends to be relative soft (usually, edema is present) compared with normal, healthy bone tissue. Accordingly, one method of treating the lesion 6 is to compact the soft bone tissue 2 at the site of the lesion 6.

Although not shown, if desired, a flowable material such as the bone cements or augmentation materials previously described could also be introduced through the implant 720 to provide additional reinforcement or mechanical stability, and/or biological activity in the region.

Figure 16A:
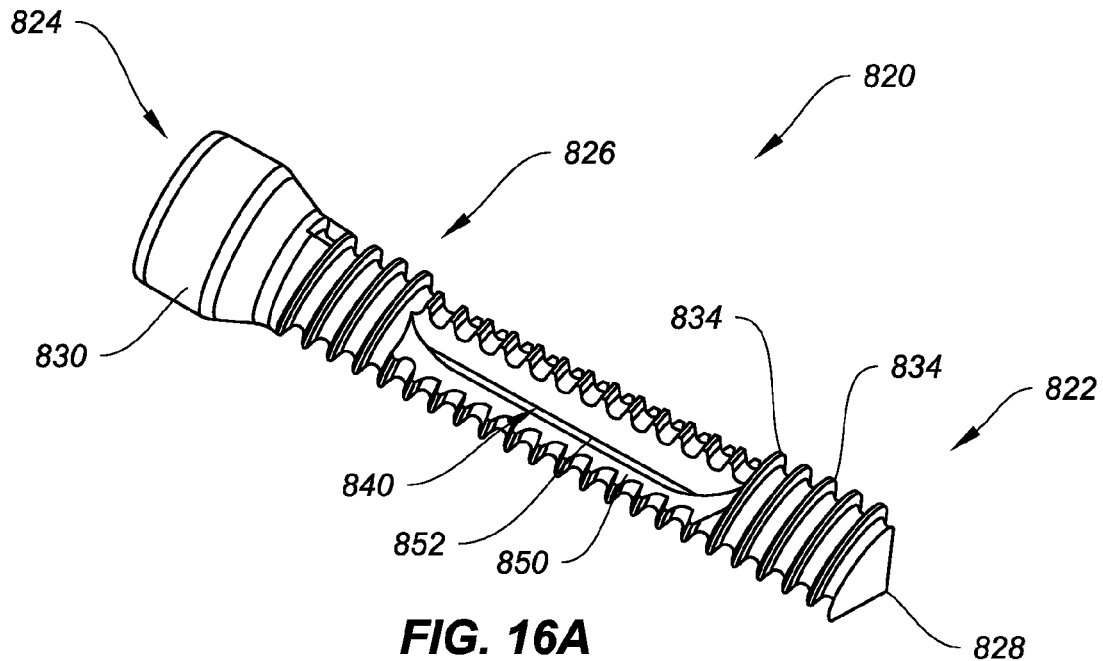
FIG. 16A is a perspective view of even still another exemplary embodiment of an implantable device of the present invention.
Figure 16B:
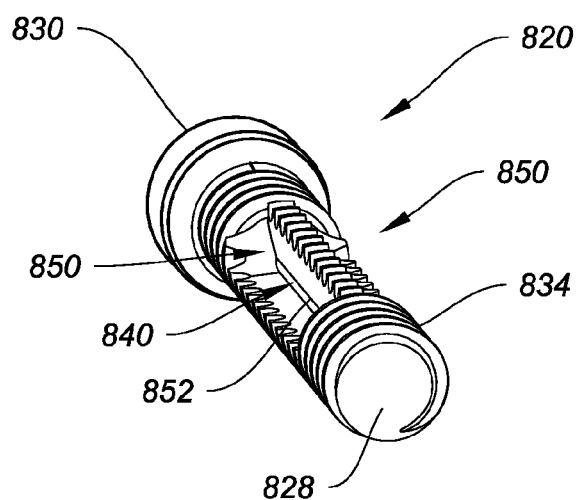
FIG. 16B is another perspective view of the implantable device of FIG. 16A.

FIGS. 16A and 16B illustrate even still another exemplary embodiment of an implantable device of the present disclosure. Implant 820 is similar to implant 320 previously described. Like implant 320, implant 820 may also include an elongate body 826 extending between a first, leading end 822 and a second, trailing end 824. Elongate body 826 may be provided with external threads 834 extending along its length. The first end 822 of the implant 820 can include a tapered nose or tip 828 to facilitate ease of insertion to the target site, while the second end 824 may include a head region 830 having an insertion tool-engaging opening (not shown). This tool-engaging opening may also extend into a central channel 840 that stretches down the length of the implant 820 a desired distance.

As FIG. 16B shows, the elongate body 826 may have a pair of segmental cutaway portions 850 that have a general appearance of approximately a quarter cross-sectional area of the cylindrical elongate body 826. The segmental cutaway portions 850 appear on opposed lateral sides of the elongate body 826. Each segmental cutaway portion 850 may intersect the central channel 840 to create a slot 852 within the segmental cutaway portion 850. The open slot 852, being in communication with the central channel 840, allows the user to introduce a flowable material, such as a bone cement or augmentation material as previously described, into the central channel 840 and allow the material to extrude out of the slots 842 away from the elongate body 826.

Figure 17:
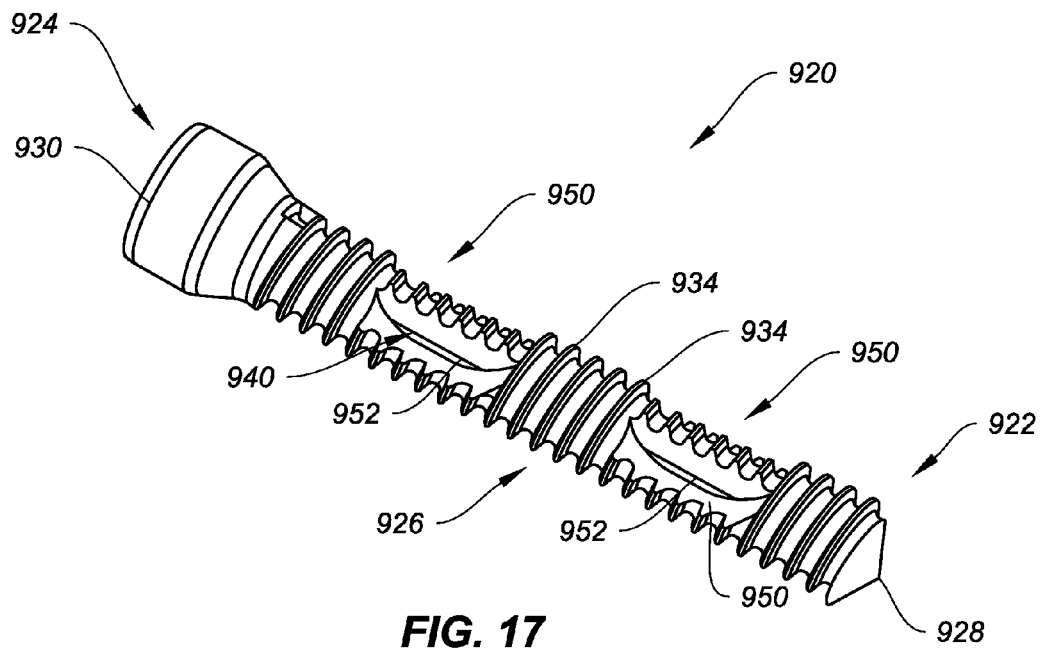
FIG. 17 is a perspective view of another exemplary embodiment of an implantable device of the present invention.

FIG. 17 illustrates yet still another exemplary embodiment of an implantable device of the present disclosure. Implant 920 shares the same structural elements and characteristics of implant 820 previously described. Implant 920 can include an elongate body 926 extending between a first, leading end 922 and a second, trailing end 924. Elongate body 926 may be provided with external threads 934 extending along its length. The first end 922 of the implant 920 can include a tapered nose or tip 928 to facilitate ease of insertion to the target site, while the second end 924 may include a head region 930 having an insertion tool-engaging opening (not shown). This tool-engaging opening may also extend into a central channel 940 that stretches down the length of the implant 920 a desired distance.

Like implant 820, the elongate body 926 may have segmental cutaway portions 950 that have a general appearance of approximately a quarter cross-sectional area of the cylindrical elongate body 926. However, in this embodiment, there may be a plurality of smaller segmental cutaway portions 950 on either of the lateral sides of the implant 920, instead of a single, longer portion 950 on each lateral side as with implant 920. In fact, each lateral side of the elongate body 926 may include two or more segmental cutaway portions 950 as desired.

Again, each segmental cutaway portion 950 may intersect the central channel 940 to create a slot 952 within the cutaway portion 950. The open slot 952, being in communication with the central channel 940, allows the user to introduce a flowable material, such as a bone cement or augmentation material as previously described, into the central channel 940 and allow the material to extrude out of the slots 952 away from the elongate body 926.

In use, it is contemplated that implants 820, 920 would be positioned below the bone defect such that the external threads 834, 934 on the elongate bodies 826, 926 face towards the defect. As described earlier, this arrangement allows the greatest surface area contact between the defect and the implants 820, 920, thereby providing better mechanical strength and structural integrity to the area to be treated. After proper placement of the implants 820, 920 relative to the defect, a flowable material may be introduced into the central channel 840, 940 of the implant 820, 920 and allowed to extrude out of the slots 852, 952 and away from the elongate bodies 826, 926.

Figure 18A:
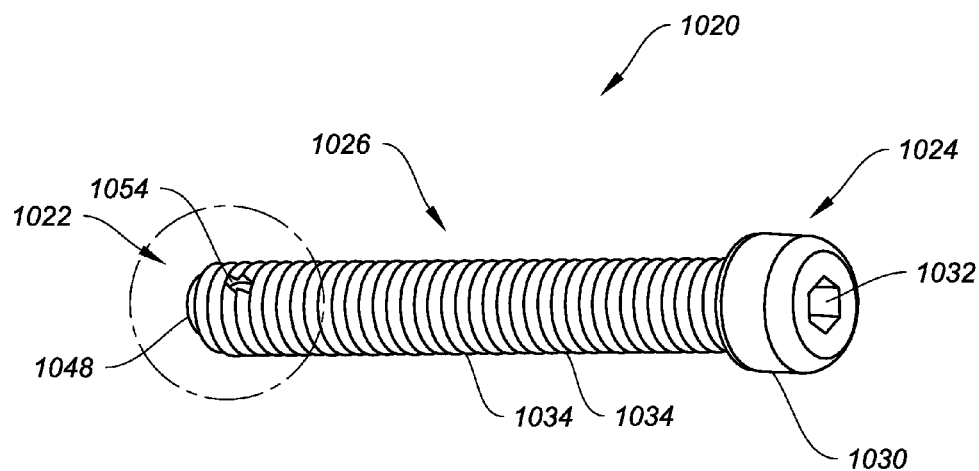
FIG. 18A is a perspective view of still another exemplary embodiment of an implantable device of the present invention.
Figure 18B:
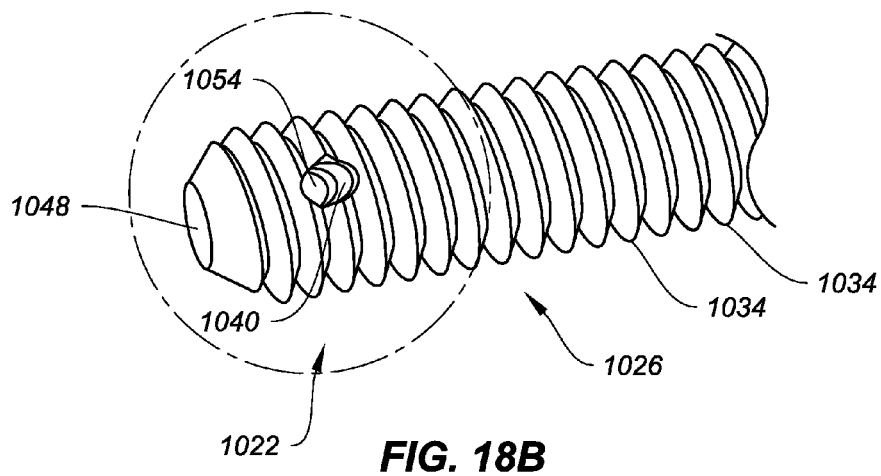
FIG. 18B is an enlarged view of one end of the implantable device of FIG. 18A.

FIGS. 18A and 18B illustrate even still another exemplary embodiment of an implantable device of the present disclosure. The implant 1020 may include a first, leading end 1022, a second, trailing end 1024, and an elongate body 1026 extending between the ends 1022, 1024. The first, leading end 1022 may terminate at a flat end surface 1048, while the second, trailing end 1024 may terminate at a head region 1030. The head region 1030 may include a tool-engaging opening 1032 for receiving an insertion tool (not shown). The tool-engaging opening 1032 may extend into a central channel 1040 that may extend into the elongate body 1026. External threads 1034 may be provided on the elongate body 1026, as shown. In addition, a side port 1054 may be provided in communication with the central channel 1040 near the first, leading end 1022.

In one exemplary method of using implant 1020, the implant 1020 may be inserted adjacent a bone defect. Then, a flowable material may be introduced through the central channel 1040 and extruded out the side port 1054 such that the flowable material is extruded near the first, leading end 1022 of the implant 1020. The flowable material may be a bone cement or augmentation material, as previously described. It is contemplated that the implant 1020 may be utilized in the same manner as described for implant 720 to compact soft bone tissue of bone 2 surrounding the lesion 6, whereupon the flowable material introduced at the first, leading end 1022 can be extruded in the area adjacent the compacted bone.

Figure 19:
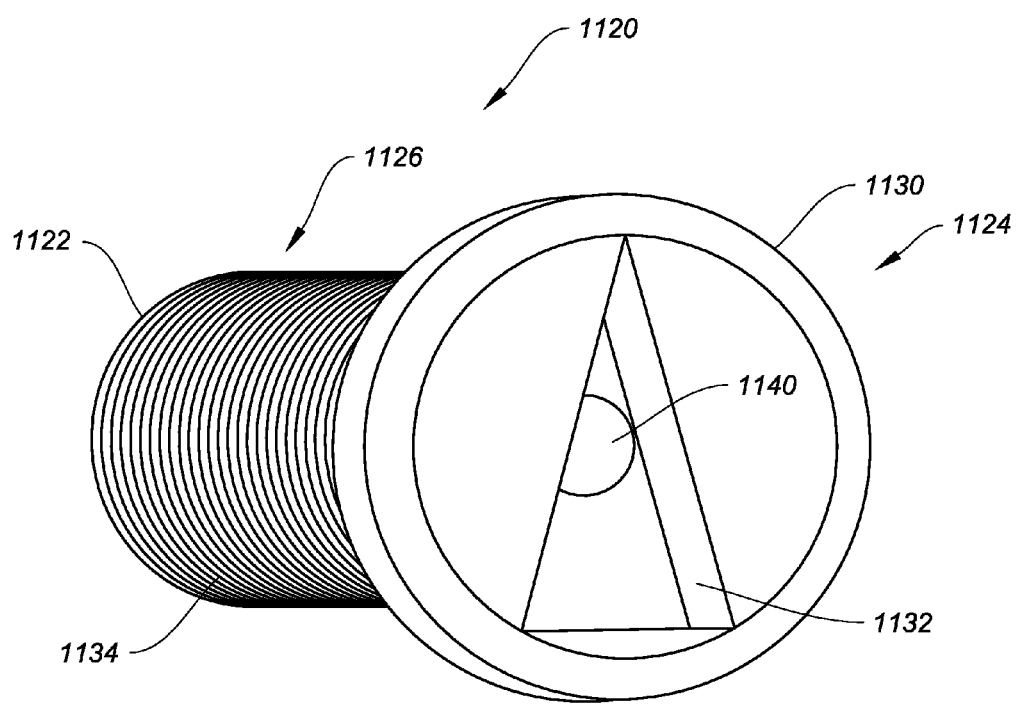
FIG. 19 is a perspective view of a second, trailing end of an implantable device of the present invention.

FIG. 19 illustrates yet another exemplary embodiment of an implantable device of the present disclosure. Implant 1120 is similar to implant 320 previously described. Like implant 320, implant 1120 may include an elongate body 1126 extending between a first, leading end 1122 and a second, trailing end 1124. Elongate body 1126 may be provided with external threads 1134 extending along its length. The second end 1124 may include a head region 1130 having a tool-engaging opening 1132 for receiving an insertion tool (not shown). This tool-engaging opening 1132 may also extend into a central channel 1140 that stretches down the length of the implant 1120 a desired distance.

In addition, the opening 1132 may have a geometry that would allow the user to determine the directionality of the implant 1120. For example, as shown, the tool-engaging opening 1132 may have a shape of an isosceles triangle. Other shapes are contemplated, and the characteristics of this shaped tool-engaging opening 1132 may be employed in any of the embodiments of the present disclosure, in order to allow directional control over the positioning of the implants into bone.

It is contemplated that the various implants described herein may be formed of any suitable biocompatible material, including metal or polymer materials. Suitable metals may include, but are not limited to, stainless steel, titanium, titanium alloys, and cobalt chrome, as examples. Porous metals may also be appropriate. The implant may also be ABS injection molded plastic, polyetheretherketone (PEEK), polyethylene (PE), or ultra high molecular weight polyethylene (UHMWPE). If desired, the implant may be bioabsorbable or bioresorbable. In some embodiments, the implant may be formed of allograft or cadaver bone, including cortical, cortico-cancellous, bi-cortical, tri-cortical, or sesamoid bone material. In other embodiments, the implant may be formed partially or wholly from a radiolucent material. For example, the implant may be formed from a material blended with a radiopaque material, such as barium sulfate. In addition, radiopaque markers may be employed with the implant for imaging possibilities.

While the elongate bodies of the implants are shown as being substantially cylindrical, it is understood that the implants may be shaped so as to have varying diameters along its length. For instance, the implants may have an overall figure "8" shape, a bowling pin shape, etc. so long as it is suitable for insertion into bone tissue and has enough structural integrity to perform its intended function of bridging a fracture or fissure, supporting bone regrowth or remodeling, and/or binding the bone tissue together to prevent further breakdown or degeneration.

The implants of the present disclosure may be used to repair bone defects in a joint region such as the knee, shoulder, ankle, hip or other joint of the patient's body. The implants may be useful, for example, in repairing an insufficiency fracture of a bone at a joint. The implants may serve as a fusion device, enabling rigid fixation at the defect site.

Alternatively, the implants may be configured to facilitate the patient's natural healing process without fusion at the defect site.

If desired, the implants may also include a biological agent. The biological agent may be included in a coating on the implant. Alternatively, the biological agent may be embedded inside the implant. Suitable biological agents may include, for example, osteogenic, osteoconductive and/or osteoinductive agents. In addition, a bioactive agent such as platelet rich plasma (PRP), bone marrow aspirate (BMA), bone morphogenic protein (BMP), demineralized bone matrix (DBM), stem cells, or allograft material, for example, may also be employed. Furthermore, a bioactive surface may be created on the implant by treating the implant with, for example, acid etching, grit blasting, plasma spraying, bioactive glass coating, photo-chemical etching, or other suitable surface treatments for creating a roughened surface.

As noted, while the implants have been described as being used with an injectable or flowable material, it is understood, however, that these implants shown and described herein may be used alone without any injectable or flowable material if so desired. In some instances where there is bone deformity, and a bone defect must be resected, it is desirable to provide a suitable implantable device that can be placed into the void left by the resected bone. The implantable device may be inserted in an open procedure, or it may be inserted in a minimally invasive procedure if the bone tissue is soft enough to accommodate the implantable device in this fashion.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. An implantable device for treating a subchondral bone defect of a bone of a joint, comprising:
    an elongate body extending between a first, leading end and a second, trailing end, the second end including a tool-receiving portion for receiving a tool, the elongate body including a central canal for receiving a flowable material, and having one or more channels in fluid communication with the central canal for dispersing the flowable material, the channels being located along one side of the elongate body;
    the elongate body further comprising a depressed, cutaway portion for containing the area where material extrudes, the one or more channels residing within the depressed, cutaway portion;
    wherein the implantable device is configured to serve as both a mechanical support to stabilize the subchondral bone defect, and as a portal to disperse the flowable material in a directionally controlled manner to the subchondral bone defect for treatment of the defect; and
    further wherein the implantable device is configured to be implanted into a subchondral level of the bone while still preserving the articular surface of the bone.

2. The device of claim 1, wherein the tool-receiving portion comprises a tab.

3. The device of claim 1, wherein the second end includes fins.

4. The device of claim 3, wherein the device is configured to be slip-fitted and press-fitted into the bone.

5. The device of claim 1, wherein the second end includes a cap.

6. The device of claim 1, further comprising external threads along a length of the elongate body.

7. The device of claim 6, wherein the depressed, cutaway portion resides within the external threads.

8. The device of claim 1, further including a flange having a surface feature for anchorage to an outer surface of the bone.

9. The device of claim 8, wherein the surface feature comprises spikes.

10. The device of claim 1, wherein the tool is an insertion tool, an injection needle, or a catheter.

11. The device of claim 1, wherein the first end is tapered.

12. The device of claim 1, wherein the flowable material is a bone cement, bone graft material, biologic agent, osteoconductive agent, osteoinductive agent, or osteogenic agent.

13. A system for treating a subchondral bone defect of a bone of a joint, comprising:
    an implantable device for insertion into bone, the device comprising an elongate body extending between a first, leading end and a second, trailing end, the second end including a tool-receiving portion for receiving a tool, the first end having a tapered tip, the elongate body including a central canal for receiving an injection tool, and having one or more channels in fluid communication with the central canal for dispersing the flowable material, the channels being located along one side of the elongate body;
    the elongate body further comprising a depressed, cutaway portion for containing the area where material extrudes, the one or more channels residing within the depressed, cutaway portion;
    wherein the implantable device is configured to serve as both a mechanical support to stabilize the subchondral bone defect, and as a portal to disperse the flowable material in a directionally controlled manner to the subchondral bone defect for treatment of the defect; and
    further wherein the implantable device is configured to be implanted into a subchondral level of the bone while still preserving the articular surface of the bone; and
    an injection tool having a hollow shaft configured for insertion through the central canal of the implantable device, the shaft being capable of receiving the flowable material, and further including one or more channels configured to align with one or more channels of the implantable device to allow extrusion of the flowable material out of the injection tool and through the one or more channels of the implantable device.

14. The system of claim 13, wherein the injection tool includes the same amount of channels as the implantable device.

15. The system of claim 13, wherein the injection tool includes less channels than the implantable device.

16. The system of claim 13, wherein the channels of the injection tool are configured in the same spatial arrangement as the channels of the implantable device.

17. The system of claim 13, wherein the channels of the injection tool are configured in a different spatial arrangement than the channels of the implantable device.

18. A system for treating a subchondral bone defect of a bone of a joint, comprising:
    a flowable material delivery device for insertion into bone, the device comprising a threaded elongate body extending between a first, leading end and a second, trailing end, the second end including a tool-receiving portion for receiving a tool, the elongate body including a central canal for receiving a flowable material, and having one or more channels in fluid communication with the central canal for dispersing the flowable material, the channels being located along one side of the elongate body;

the elongate body further comprising a depressed, cutaway portion for containing the area where material extrudes, the one or more channels residing within the depressed, cutaway portion;

wherein the implantable device is configured to serve as both a mechanical support to stabilize the subchondral bone defect, and as a portal to disperse the flowable material in a directionally controlled manner to the subchondral bone defect for treatment of the defect; and further wherein the implantable device is configured to be implanted into a subchondral level of the bone while still preserving the articular surface of the bone; and an inserter tool having a handle extending into a shaft and terminating at a device-attachment end, the device-attachment end being configured to attach to the second end of the delivery device.

19. The system of claim 18, further including a protection sleeve including a tubular body having a handle at one end, and terminating at a bone-contacting surface at an opposite end, the tubular body including a threaded channel configured to threadedly receive the delivery device.

20. The system of claim 18, wherein the bone-contacting surface of the protection sleeve is smooth.

21. The system of claim 18, wherein the bone-contacting surface of the protection sleeve is roughened to enhance bone attachment.

* * * * *